US011318194B2

(12) United States Patent
Gong et al.

(10) Patent No.: US 11,318,194 B2
(45) Date of Patent: May 3, 2022

(54) VACCINE AGAINST NECROTIC ENTERITIS IN POULTRY

(71) Applicant: Her Majesty the Queen in Right of Canada, as Represented by the Minister of Agriculture and Agri-Food, Guelph (CA)

(72) Inventors: Jianhua Gong, Guelph (CA); Dion Lepp, Guelph (CA)

(73) Assignee: HER MAJESTY THE QUEEN IN RIGHT OF CANADA, AS REPRESENTED BY THE MINISTER OF AGRICULTURE AND AGRI-FOOD, Guelph (CA)

(*) Notice: Subject to any disclaimer, the term of this patent is extended or adjusted under 35 U.S.C. 154(b) by 0 days.

(21) Appl. No.: 16/616,619

(22) PCT Filed: May 31, 2018

(86) PCT No.: PCT/CA2018/050643
§ 371 (c)(1),
(2) Date: Nov. 25, 2019

(87) PCT Pub. No.: WO2018/218360
PCT Pub. Date: Dec. 6, 2018

(65) Prior Publication Data
US 2020/0093913 A1 Mar. 26, 2020

Related U.S. Application Data

(60) Provisional application No. 62/513,001, filed on May 31, 2017.

(51) Int. Cl.

| | |
|---|---|
| *A61K 39/08* | (2006.01) |
| *A61K 39/00* | (2006.01) |
| *C07K 16/12* | (2006.01) |
| *G01N 33/569* | (2006.01) |

(52) U.S. Cl.
CPC .......... *A61K 39/08* (2013.01); *C07K 16/1282* (2013.01); *G01N 33/56911* (2013.01); *A61K 2039/552* (2013.01); *A61K 2039/55577* (2013.01); *A61K 2039/70* (2013.01); *G01N 2333/33* (2013.01)

(58) Field of Classification Search
None
See application file for complete search history.

(56) References Cited

U.S. PATENT DOCUMENTS

2002/0019517 A1 * 2/2002 Koide .................... C07K 16/40 530/387.1

FOREIGN PATENT DOCUMENTS

| | | | |
|---|---|---|---|
| WO | 0104148 | A2 | 1/2001 |
| WO | 2011113801 | A1 | 9/2011 |
| WO | WO 2020/035741 | A2 * | 7/2018 |

OTHER PUBLICATIONS

Rodgers et al. Infect. Immun. 79: 3096-3105, 2011.*
Jost et al. Vet. Microbiol. 115: 173-182, 2006.*
Clostridium perfringens putative collagen adhesin protein_id ALJ54440.1 encoded by the sequence with accession No. KT749987, Nov. 25, 2015.*
Skolnick et al. Trends in Biotechnology, 18: 34-39, 2000.*
Rudinger J. In: Peptide Hormones. (Ed) JA Parsons, University Park Press, pp. 1-7, 1976.*
Greenspan et al. Nature Biotechnology 17: 936-937, 1999.*
Ton-That, H., et al., "Sortases and pilin elements involved in pilus assembly of Corynebacterium diphtheriae." Molecular Microbiology, 2004, 53(1): 251-261.
"Putative collagen adhesin [Clostridium perfringens]". GenBank Protein Accession No. ALJ54440, Nov. 25, 2015, [online] [retrived on Jul. 23, 2018]. Retrieved from the Internet: https://www.ncbi.nlm.nih.gov/protein/ALJ54440.
"Hypothetical protein BXT94_03025 [Clostridium perfringens]". GenBank Protein Accession No. AQW25808, Mar. 3, 2017, [online] [retrieved on Jul. 23, 2018]. Retrieved from the Internet: https:www.ncbi.nlm.nih.gov/protein/AQW25808.
"Hypothetical protein BXT94_03035 [Clostridium perfringens]". GenBank Protein Accession No. AQW25810, Mar. 3, 2017, [online] [retrieved on Jul. 23, 2018]. Retrieved from the Internet: https://www.ncbi.nlm.nih.gov/protein/AQW25810.
Lepp, D., et al., "Identification of Accessory Genome Regions in Poultry Clostridium perfringens Isolates Carrying the netB Plasmid." Journal of bacteriology, 2013,195(6): 1152-1166.
Prescott, J.F., et al., "The pathogenesis of necrotic enteritis in chickens: what we know and what we need to know: a review." Avian Pathology, 2016, 45(3): 288-294.
Wade, B., et al., "The adherent abilities of Clostridium perfringens strains are critical for the pathogenesis of avian necrotic enteritis." Veterinary microbiology, 2016, 197: 53-61.
Hypthetical Protein [Clostridium perfringens], Database Accession No. WP_057230739.

(Continued)

*Primary Examiner* — Sarvamangala Devi
(74) *Attorney, Agent, or Firm* — Saliwanchik, Lloyd & Eisenschenk

(57) ABSTRACT

An immunogenic polypeptide selected from an isolated *Clostridium perfringens* pilus polypeptide, a variant of the pilus polypeptide; a fragment of the pilus polypeptide; and a fragment of the variant, is useful for the preparation of a vaccine for the treatment or prevention of enteric necrosis in poultry. The isolated *Clostridium perfringens* pilus polypeptide includes an assembled pilus or the pilus subunits CnaA, FimA and/or FimB.

13 Claims, 8 Drawing Sheets

Specification includes a Sequence Listing.

(56) References Cited

OTHER PUBLICATIONS

Lepp, D., et al., "Immunization with subunits of a novel pilus produced by virulent Clostridium perfringens strains confers partial protection against necrotic enteritis in chickens." Veterinary Microbiology, 2019, 230: 7-13.

Lepp, D., et al., "Clostridium perfringens Produces an Adhesive Pilus Required for the Pathogenesis of Necrotic Enteritis in Poultry." Journal of Bacteriology, Apr. 2021, 203(7): e00578-20, pp. 1-14.

Wade, B., et al., "Binding of Clostridium perfringens to collagen correlates with the ability to cause necrotic enteritis in chickens." Veterinary Microbiology, 2015, 180(3-4): 299-303.

Wade, B., et al., "Binding of Clostridium perfringens to collagen correlates with the ability to cause necrotic enteritis in chickens." Veterinary Microbiology, Clostridium perfingens. Database Accession No. A0A0N7IDU3.

* cited by examiner

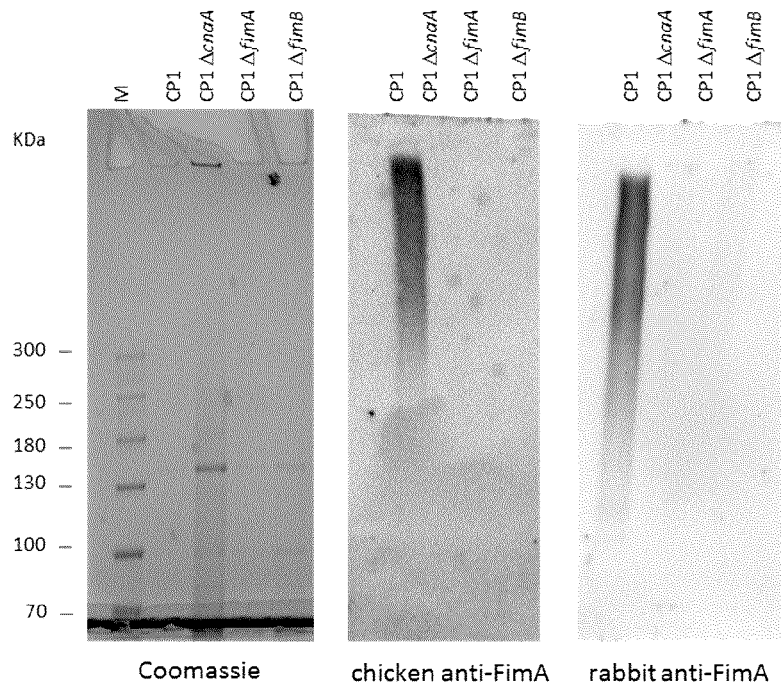
Coomassie     chicken anti-FimA     rabbit anti-FimA
FIG. 8A     FIG. 8B     FIG. 8C
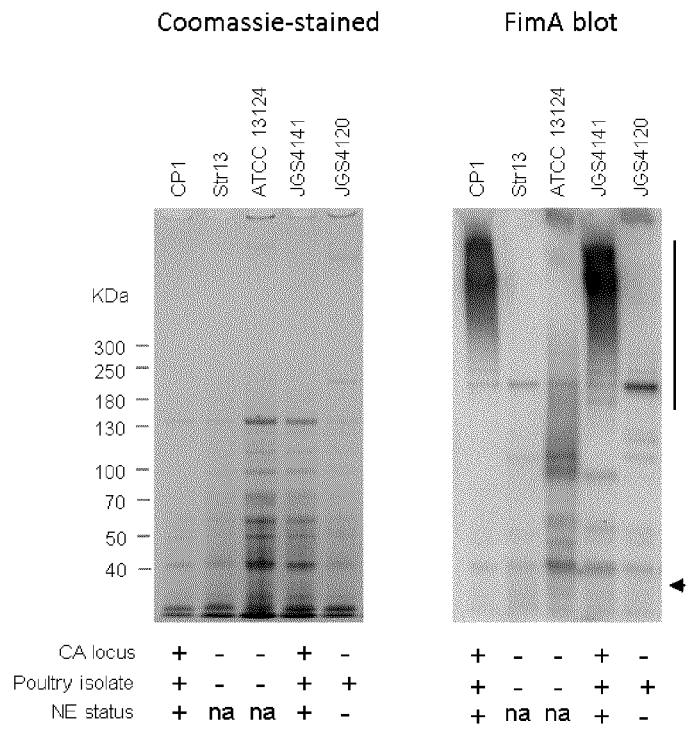
FIG. 9A     FIG 9B

SEQUENCE LISTING

<160> NUMBER OF SEQ ID NOS: 16

<210> SEQ ID NO 1
<211> LENGTH: 2091
<212> TYPE: DNA
<213> ORGANISM: Clostridium perfringens

<400> SEQUENCE: 1

```
atgaaaataa ataaaaaaat ttttagcatg ctatttatgg ttattgtact ttttacatgc      60
atatcatcaa atttttctgt ttctgcttct tctattcaaa gaggaagaga tatcagtaat     120
gaggtagtta caagcctagt ggctactcca aatagtataa atgatggtgg aaacgttcag     180
gttcgtttgg aatttaaaga aaatcatcaa agaaatatac aaagtggaga tactataact     240
gtcaaatgga caaattcagg ggaagtattt tttgaaggat atgaaaaaac aattccactt     300
tatataaaag accaaaatgt tggtcaagca gtaatagaga aaacaggtgc aacacttaca     360
tttaatgata aaatagataa attagatgat gttggtggat gggcaacatt tactttgcaa     420
ggaagaaaca ttacctcagg taatcatgaa cacacaggaa tagcatatat tatatctggt     480
tcaaagcggg cagatgtaaa tataaccaaa ccagaatcag gtacaactag tgtattctat     540
tataaaacag gtagtatgta taccaatgat acaaatcatg tcaattggtg gttactggtg     600
aatccaagca aggtatattc tgaaaaaaac gtttatattc aagatgaaat ccaaggcgga     660
caaacattag aacctgattc ttttgaaata gtagtaactt ggtatgatgg ttatgtagaa     720
aagtttaaag gaaaagaagc gataagggaa ttccataata aatatccaaa ttcaaatata     780
tcggtatcag aaaataaaat aacagtaaac atttcacaag aggattccac acaaaagttt     840
attaatattt tttataaaac taagattaca aatccgaaac aaaaagaatt cgttaataat     900
acaaaagcat ggtttaaaga gtataataag ccagctgtaa atggagaatc ctttaaccat     960
agcgtacaaa atattaatgc agatgctgga gttaatggaa ctgtaaaagg cgaattaaaa    1020
atcataaaaa cattaaaaga taaagtatt ccaattaaag atgttcagtt taagatgaga    1080
agagttgata tacagttat caaagatggt aaaaaagaat tattactaac aactgatgat    1140
aaaggtattg caaatgtaaa aggtcttcct gtaggaaaat atgaagtaaa agagatttca    1200
gctccagaat ggattgcttt taatcctctt attgcaccaa aattggaatt cacaatatca    1260
gatcaggaca cagaaggcaa attgtgggct gttgaaaatg aattaaagac aatttcaatt    1320
ccggttgaaa aggtctgggt aggacaaact agtgaacgag cagaaatcaa gcttttgca    1380
```

```
gatggtattg aagtagacaa agtgatttta aatgcagata acaattggaa acacacattt    1440
gaaaataaac ctgaatataa ttcagaaaca aaacagaaaa tcaattattc tgtgtcagag    1500
acaactattt ctggatatga aagcaatatc acaggcgatg ctaagaatgg ttttattgta    1560
accaatacag aacttcctga tttgactatt ggtaaagaag ttataggaga attgggtgac    1620
aagacgaagg tatttaactt tgagcttaca ttaaagcaag cagatggaaa gcctatcaat    1680
ggtaaattta attacattgg tagtgtagat gacaggtaca aaaagaaag cataaagcct    1740 tctgatggtg agattacttt tatagaagga aaagcaacta taactttatc acatggacaa    1800
gagattacaa tcaaggattt accatatggg gttacatata agttatgga aaaagaagct    1860 aatgaaaatg gctatttaac tacctataat ggaaataacg aagtcacaac aggtgaattg    1920
aaacaggata caaagtaca ggtagttaac aacaaagagt ttgttccaac aactggtata    1980
tcaaccacaa cagagcaagg tacaatggtt ggaatggtga ttttttctat aggaatactt    2040
atggtcatga ttgtagttct tttacaattg aataaaggac tgaaaagatg a            2091
```

<210> SEQ ID NO 2
<211> LENGTH: 1074
<212> TYPE: DNA
<213> ORGANISM: Clostridium perfringens

<400> SEQUENCE: 2

```
atgataaaca agaaaaaatt aagtgcatta ttattaagtg gagcaatgtt tatgagtatg      60
aatacaaatg tattcgcatc aaatttacct tctggagggg tagaaggtac agaacagaat     120
cctgcaaaag caacaattac aaagaatttt gaatttccag aagtattaa tacacctagt     180 gcaacattca gtttacagc agaaaaaata actaatgatg cgccagatgc aacaattgga     240
gatattaatt atacacaagg ggataatgga actttatcaa atggaaaata tagtgtaaag     300
aaaacaactg aaattacttt tggaaatttc ccacatgcag agaatatga ttataatgta     360 aagaaacga atgagggagt aggtggtatt acatatgata caaagaata caaagttcat     420 gtgtatgttg caaatagtaa cgctatggat ggaaaaactt atgtaaaagc cattacatca     480
gaaaatggag gtgaaaagc tccaattgag tttgttaata catataaaaa ggacacttct     540
ttacttatag aaaagaatgt aataggagat ttagctgact aacaaaaaca gtttgagttt     600
cagattaatt taaaaaatc agcaacatct gacataacaa aattcgaagg aaatattatt     660
agaaaagatg gtaaaataga gcctgtaaca tatacagctg aaaatacaga aacttttaaa     720
ttagcaaatg gagataaact taagtttgaa agtattccag caggaacaaa atatgaagta     780
aaagagatag gtgctagtga tggatataca ccttctataa cagtaattga aaatggaaat     840
gagacttcta ataatcgtac ggtagctgaa aaagatggta tcatctaa gtcaaattct     900 aatgataact taattggtga aggtgaaaac aaagtaacat ttacaaacac atataatgac     960
aaacctatca caggtattgt tatgaataat attccatta ttctaatgat tagttttgct    1020
gtccttggat ttggtgctt agctattata aaaagacgta aaactataag ataa           1074
```

<210> SEQ ID NO 3
<211> LENGTH: 660
<212> TYPE: DNA
<213> ORGANISM: Clostridium perfringens

<400> SEQUENCE: 3

```
atggaaacaa agaaaataag aaacaaaatc cttatggcta tcgtagcatt gagctttata       60
ttgcttccaa acactagagt atatgctact gaaaatacag caaatattcc tttgatagtt     120
```

```
agacaggaat ttaatgtata tacgaaagat tcaaaagcaa tagacatgat tggaaaatac      180
gagctaaagg caataagtga aaatgcccct atgccagaag aaagtaaaaa tggaagtttt      240
atctttaata tagatggaaa tgataagcag tttactattc cattagctta tacacatggt      300
ggtgtgtata tctatcaaat tcaacagata acgcaatcta aagataatta catatatgat      360
aaaaatagct ataagataac tgtatatgta aaaaatgcag aaaataatca tttaatacca      420
caaattattg tgaaaaatga aaataatgaa aaatgtgaag aaatatgttt ttataacatt      480
tacaaacaaa aaaataaaat taatgagatt tctaaaacac catataagcc aaatggaata      540
aatgttccta aaacaggcga taccacaaac attggatttt atattgtaat acttataatt      600
tcacttggat tacttgtggt attgaaatgg aaagaatata aaagagaaa aaaagaataa      660

<210> SEQ ID NO 4
<211> LENGTH: 2088
<212> TYPE: DNA
<213> ORGANISM: Artificial Sequence
<220> FEATURE:
<223> OTHER INFORMATION: cnaA codon optimized

<400> SEQUENCE: 4
atgaagatca acaagaagat cttcagcatg ttatttatgg tcattgtgct gttcacctgt       60
atcagctcta acttcagtgt gagcgcgtca agcatccagc gcggccggga catcagcaac      120
gaggtggtga catcgctcgt agctaccccg aatagcatca cgatggtgg taacgtccaa      180 gtgcgtctgg aatttaaaga gaatcaccag cggaacattc agtccggcga cacgattacg      240
gtcaaatgga ctaactcagg tgaggtcttt tttgaaggct acgaaaaaac catcccgctg      300
tatatcaagg atcagaacgt tggccaggcg gttattgaaa aaaccggtgc aacattaaca      360
ttcaacgata agatcgacaa attagatgat gtcggcggct gggccacatt cacgctccag      420
ggtcgcaata ttacttcagg aaatcatgag catactggta ttgcgtacat tatctcgggt      480
agcaaacgtg cggacgttaa catcacaaaa cctgaatccg aacaacgtc tgtgttttac      540 tacaagacgg gttcgatgta caccaatgac acaaatcatg tgaattggtg gctgctggtt      600
aacccgagca agtatactc tgagaaaaat gtctatattc aggatgaaat tcaaggcggt      660
cagaccctgg agccggacag ttttgaaatc gtcgttacat ggtacgatgg ttatgtggaa      720
aaatttaaag gtaaagaagc gatccgggag ttccacaata aatatccgaa tagtaatatc      780
tcggtcagtg aaaataaaat cacggtaaat atttcgcaag aagattccac ccaaaaattc      840
attaacatct tttacaagac taaaatcacc aacccgaagc agaaagaatt tgtaaacaac      900
accaaagcct ggttcaaaga gtacaataag ccggcggtta acggtgaaag ttttaatcac      960
agtgtgcaga tatcaacgc agatgccggg gtaaatggta ctgttaaagg tgaattgaaa     1020
attatcaaaa ccctgaaaga taaagtatt ccgatcaagg atgtgcagtt aagatgcgc      1080 cgcgtggata taccgttat aaagacggc aagaaagagc tgctgttgac acagatgat      1140 aaagggattg caaacgtgaa aggtctgcca gtcgggaaat acgaagtcaa agaaatcagt     1200
gcgcctgagt ggatcgcctt caatccactg attgcgccca acttgaatt tacgatcagc     1260 gatcaagaca cagaggggaa attatgggca gtggaaaacg aactcaaaac catctcgatt     1320
ccggtcgaaa aagtctgggt aggtcagacg agtgaacggg cggagatcaa actgtttgcg     1380
gatggaattg aagttgataa ggtgatcctg aacgcgata taattggaa gcacaccttt     1440 gagaataaac ccgaatataa ctccgagact aaacaaaaaa tcaactatag tgtgagcgaa     1500
```

| | |
|---|---|
| actaccatca gtggctatga atcaaatatt actggcgatg cgaaaaacgg atttattgtc | 1560 |
| accaacacag aactgcctga tttgacgatc gggaaagagg taatcggcga actcggcgat | 1620 |
| aaaaccaagg tattcaactt tgaactgaca cttaagcagg ctgacggaaa gcccattaac | 1680 |
| gggaaattta actatattgg ttcggtggat gatcgttata agaaggaatc gattaagcct | 1740 |
| agcgatgggg aaattacgtt catcgaggga aaagcaacga ttaccctctc ccacggacaa | 1800 |
| gagatcacca ttaaggacct tccgtatggt gtgacctata agtcatgga aaagaagcc | 1860 |
| aacgagaatg atatttaac cacttacaac ggaaataacg aagtcaccac cggggagttg | 1920 |
| aaacaggata cgaaagtaca agtggttaat aataaagaat tcgtcccgac aaccgggatc | 1980 |
| agcaccacca ccgaacaggg aaccatggtc gggatggtga tctttagcat cggtattctc | 2040 |
| atggtaatga ttgtcgttct gctgcagctg aataaaggac tgaaacgc | 2088 |

<210> SEQ ID NO 5
<211> LENGTH: 1086
<212> TYPE: DNA
<213> ORGANISM: Artificial Sequence
<220> FEATURE:
<223> OTHER INFORMATION: fimA codon optimized

<400> SEQUENCE: 5

| | |
|---|---|
| atgattaata aaagaaact gtcggcgctg ctcttaagcg gggccatgtt tatgagcatg | 60 |
| aacacgaatg tgttcgcgtc taacctccca tcgggtggtg tggagggcac cgaacaaaac | 120 |
| ccagcgaaag cgacaatcac gaaaaacttc gagtttccgg aaggtattaa tacacccagc | 180 |
| gcgacattca aatttaccgc cgaaaaaatt accaacgatg cgccggatgc tactattggc | 240 |
| gacatcaatt tacccaagg tgataatggg acgttaagca atggcaaata cagtgtgaaa | 300 |
| aagactaccg agattacctt cgggaacttc ccgcatgctg gtgagtatga ttataacgtc | 360 |
| aaagaaacca atgaaggcgt gggtggcatt acttacgata cgaaagaata taagttcat | 420 |
| gtgtatgtgg ccaactcaaa tgcgatggac ggtaagacat atgttaaagc gattactagc | 480 |
| gaaaatggcg gggaaaaagc accgatcgaa ttcgttaaca cctataaaaa agatacgtcg | 540 |
| ttactgattg aaaaaaatgt aattggcgat ctggcagacc tcaccaaaca gtttgagttt | 600 |
| caaatcaact tgaaaagag cgcgactagt gatattacca agtttgaagg taacattatt | 660 |
| cgcaaagacg gtaagattga acccgtgacc tataccgcgg aaaataccga gacctttaag | 720 |
| ttagccaacg gagacaagtt aaaattcgag tccatccccg ccggtacaaa atatgaagtc | 780 |
| aaggaaatcg gggcgagcga tgggtacacg ccctcaatca ccgttatcga aaatggcaac | 840 |
| gaaacctcaa ataaccgcac tgtagccgaa aaagatggaa tctctagcaa aagcaactcg | 900 |
| aacgacaatt taatcggcga aggcgaaaat aaagtgacct taccaataca gtacaacgat | 960 |
| aaaccaatca cgggaatcgt aatgaataat attccgttca ttcttatgat tagctttgcc | 1020 |
| gttcttggct tcggtgcatt agcgatcatt aaacgccgca aaaccatccg ccccatcgat | 1080 |
| acgcgt | 1086 |

<210> SEQ ID NO 6
<211> LENGTH: 624
<212> TYPE: DNA
<213> ORGANISM: Artificial Sequence
<220> FEATURE:
<223> OTHER INFORMATION: fimB codon optimized

<400> SEQUENCE: 6

| | |
|---|---|
| atggctattg ttgctttgtc atttatcctg ctcccgaata cccgggtcta tgcgacggag | 60 |

```
aacaccgcta atatcccgtt aattgtacgc caagaattta atgtttacac taaagattct      120
aaagccattg acatgatcgg aaaatatgaa ttaaaagcca tttctgagaa cgctcccatg      180
ccggaggaat caaaaaatgg tagctttatt tttaacatcg acggtaatga taaacagttt      240
actattccgc tggcgtacac tcacggtggc gtctacatct atcaaatcca gcaaattacc      300
cagagcaagg ataactacat ctacgataaa acagctata aaatcacggt atatgtcaag       360
aacgcagaaa acaatcatct gatcccgcag attattgtaa aaaatgagaa caatgaaaaa      420
tgtgaagaaa tctgcttcta caatatctac aaacagaaaa acaagatcaa tgagatctct      480 aaaacccccct ataagccgaa tggtattaat gtcccgaaaa cgggtgatac cacgaacatc     540
ggattctaca ttgtgatctt gattatttcc ctgggcctgc tggtggtctt gaagtggaaa      600
gaatataaaa aacgtaagaa ggaa                                             624

<210> SEQ ID NO 7
<211> LENGTH: 1887
<212> TYPE: DNA
<213> ORGANISM: Artificial Sequence
<220> FEATURE:
<223> OTHER INFORMATION: cnaA truncated

<400> SEQUENCE: 7
tcaagcatcc agcgcggccg ggacatcagc aacgaggtgg tgacatcgct cgtagctacc       60
ccgaatagca tcaacgatgg tggtaacgtc caagtgcgtc tggaatttaa agagaatcac      120
cagcggaaca ttcagtccgg cgacacgatt acggtcaaat ggactaactc aggtgaggtc      180
ttttttgaag gctacgaaaa aaccatcccg ctgtatatca aggatcagaa cgttggccag      240
gcggttattg aaaaaaccgg tgcaacatta acattcaacg ataagatcga caaattagat      300
gatgtcggcg gctgggccac attcacgctc cagggtcgca atattacttc aggaaatcat      360
gagcatactg gtattgcgta cattatctcg ggtagcaaac gtgcggacgt taacatcaca      420
aaacctgaat ccggaacaac gtctgtgttt tactacaaga cgggttcgat gtacaccaat      480
gacacaaatc atgtgaattg gtggctgctg gttaacccga gcaaagtata ctctgagaaa      540
aatgtctata ttcaggatga aattcaaggc ggtcagaccc tggagccgga cagttttgaa      600
atcgtcgtta catggtacga tggttatgtg gaaaaattta aggtaaaga agcgatccgg       660 gagttccaca taaatatcc gaatagtaat atctcggtca gtgaaaataa aatcacggta       720
aatatttcgc aagaagattc cacccaaaaa ttcattaaca tcttttacaa gactaaaatc      780
accaacccga agcagaaaga atttgtaaac aacaccaaag cctggttcaa agagtacaat      840
aagccggcgg ttaacggtga agtttttaat cacagtgtgc agaatatcaa cgcagatgcc      900
ggggtaaatg gtactgttaa aggtgaattg aaaattatca aaaccctgaa agataaaagt      960
attccgatca aggatgtgca gtttaagatg cgccgcgtgg ataataccgt tattaaagac     1020
ggcaagaaag agctgctgtt gaccacagat gataaaggga ttgcaaacgt gaaaggtctg     1080
ccagtcggga atacgaagt caaagaaatc agtgcgcctg agtggatcgc cttcaatcca      1140
ctgattgcgc ccaaacttga atttacgatc agcgatcaag acacagaggg gaaattatgg     1200
gcagtggaaa acgaactcaa aaccatctcg attccggtcg aaaaagtctg gtaggtcag      1260 acgagtgaac gggcggagat caaactgttt gcggatggaa ttgaagttga taggtgatc      1320 ctgaacgcgg ataataattg gaagcacacc tttgagaata aacccgaata taactccgag     1380
actaaacaaa aaatcaacta tagtgtgagc gaaactacca tcagtggcta tgaatcaaat     1440
```

| | |
|---|---|
| attactggcg atgcgaaaaa cggatttatt gtcaccaaca cagaactgcc tgatttgacg | 1500 |
| atcgggaaag aggtaatcgg cgaactcggc gataaaacca aggtattcaa ctttgaactg | 1560 |
| acacttaagc aggctgacgg aaagcccatt aacgggaaat ttaactatat tggttcggtg | 1620 |
| gatgatcgtt ataagaagga atcgattaag cctagcgatg gggaaattac gttcatcgag | 1680 |
| ggaaaagcaa cgattaccct ctcccacgga caagagatca ccattaagga ccttccgtat | 1740 |
| ggtgtgacct ataaagtcat ggaaaaagaa gccaacgaga atggatattt aaccacttac | 1800 |
| aacggaaata cgaagtcac caccggggag ttgaaacagg atacgaaagt acaagtggtt | 1860 |
| aataataaag aattcgtccc gacaacc | 1887 |

<210> SEQ ID NO 8
<211> LENGTH: 894
<212> TYPE: DNA
<213> ORGANISM: Artificial Sequence
<220> FEATURE:
<223> OTHER INFORMATION: fimA truncated

<400> SEQUENCE: 8

| | |
|---|---|
| tctaacctcc catcgggtgg tgtggagggc accgaacaaa acccagcgaa agcgacaatc | 60 |
| acgaaaaact tcgagtttcc ggaaggtatt aatacacccg cgcgacatt caaatttacc | 120 |
| gccgaaaaaa ttaccaacga tgcgccggat gctactattg gcgacatcaa ttatacccaa | 180 |
| ggtgataatg gacgttaag caatggcaaa tacagtgtga aaaagactac cgagattacc | 240 |
| ttcgggaact tcccgcatgc tggtgagtat gattataacg tcaaagaaac caatgaaggc | 300 |
| gtgggtggca ttacttacga tacgaaagaa tataagttc atgtgtatgt ggccaactca | 360 |
| aatgcgatgg acgtaagac atatgttaaa gcgattacta gcgaaaatgg cggggaaaaa | 420 |
| gcaccgatcg aattcgttaa cacctataaa aagatacgt cgttactgat tgaaaaaaat | 480 |
| gtaattggcg atctggcaga cctcaccaaa cagtttgagt ttcaaatcaa cttgaaaaag | 540 |
| agcgcgacta gtgatattac caagtttgaa ggtaacatta ttcgcaaaga cggtaagatt | 600 |
| gaacccgtga cctataccgc ggaaaatacc gagacctta agttagccaa cggagacaag | 660 |
| ttaaaattcg agtccatccc cgccggtaca aaatatgaag tcaaggaaat cggggcgagc | 720 |
| gatgggtaca cgccctcaat caccgttatc gaaaatggca cgaaacctc aaataaccgc | 780 |
| actgtagccg aaaaagatgg aatctctagc aaaagcaact cgaacgacaa tttaatcggc | 840 |
| gaaggcgaaa ataagtgac ctttaccaat acgtacaacg ataaaccaat cacg | 894 |

<210> SEQ ID NO 9
<211> LENGTH: 468
<212> TYPE: DNA
<213> ORGANISM: Artificial Sequence
<220> FEATURE:
<223> OTHER INFORMATION: fimB truncated

<400> SEQUENCE: 9

| | |
|---|---|
| acggagaaca ccgctaatat cccgttaatt gtacgccaag aatttaatgt ttacactaaa | 60 |
| gattctaaag ccattgacat gatcggaaaa tatgaattaa aagccatttc tgagaacgct | 120 |
| cccatgccgg aggaatcaaa aaatggtagc tttatttta acatcgacgg taatgataaa | 180 |
| cagtttacta ttccgctggc gtacactcac ggtggcgtct acatctatca aatccagcaa | 240 |
| attacccaga gcaaggataa ctacatctac gataaaaaca gctataaaat cacggtatat | 300 |
| gtcaagaacg cagaaaacaa tcatctgatc ccgcagatta ttgtaaaaaa tgagaacaat | 360 |
| gaaaaatgtg aagaaatctg cttctacaat atctacaaac agaaaaacaa gatcaatgag | 420 | atctctaaaa ccccctataa gccgaatggt attaatgtcc cgaaaacg    468

<210> SEQ ID NO 10
<211> LENGTH: 696
<212> TYPE: PRT
<213> ORGANISM: Clostridium perfringens

<400> SEQUENCE: 10

| Met | Lys | Ile | Asn | Lys | Lys | Ile | Phe | Ser | Met | Leu | Phe | Met | Val | Ile | Val |
|---|---|---|---|---|---|---|---|---|---|---|---|---|---|---|---|
| 1 | | | | 5 | | | | | 10 | | | | | 15 | |

| Leu | Phe | Thr | Cys | Ile | Ser | Ser | Asn | Phe | Ser | Val | Ser | Ala | Ser | Ser | Ile |
| | | | 20 | | | | | 25 | | | | | 30 | | |

| Gln | Arg | Gly | Arg | Asp | Ile | Ser | Asn | Glu | Val | Val | Thr | Ser | Leu | Val | Ala |
| | | 35 | | | | | 40 | | | | | 45 | | | |

| Thr | Pro | Asn | Ser | Ile | Asn | Asp | Gly | Gly | Asn | Val | Gln | Val | Arg | Leu | Glu |
| | 50 | | | | | 55 | | | | | 60 | | | | |

| Phe | Lys | Glu | Asn | His | Gln | Arg | Asn | Ile | Gln | Ser | Gly | Asp | Thr | Ile | Thr |
| 65 | | | | | 70 | | | | | 75 | | | | | 80 |

| Val | Lys | Trp | Thr | Asn | Ser | Gly | Glu | Val | Phe | Phe | Glu | Gly | Tyr | Glu | Lys |
| | | | | 85 | | | | | 90 | | | | | 95 | |

| Thr | Ile | Pro | Leu | Tyr | Ile | Lys | Asp | Gln | Asn | Val | Gly | Gln | Ala | Val | Ile |
| | | | 100 | | | | | 105 | | | | | 110 | | |

| Glu | Lys | Thr | Gly | Ala | Thr | Leu | Thr | Phe | Asn | Asp | Lys | Ile | Asp | Lys | Leu |
| | | 115 | | | | | 120 | | | | | 125 | | | |

| Asp | Asp | Val | Gly | Gly | Trp | Ala | Thr | Phe | Thr | Leu | Gln | Gly | Arg | Asn | Ile |
| | 130 | | | | | 135 | | | | | 140 | | | | |

| Thr | Ser | Gly | Asn | His | Glu | His | Thr | Gly | Ile | Ala | Tyr | Ile | Ile | Ser | Gly |
| 145 | | | | | 150 | | | | | 155 | | | | | 160 |

| Ser | Lys | Arg | Ala | Asp | Val | Asn | Ile | Thr | Lys | Pro | Glu | Ser | Gly | Thr | Thr |
| | | | | 165 | | | | | 170 | | | | | 175 | |

| Ser | Val | Phe | Tyr | Tyr | Lys | Thr | Gly | Ser | Met | Tyr | Thr | Asn | Asp | Thr | Asn |
| | | | 180 | | | | | 185 | | | | | 190 | | |

| His | Val | Asn | Trp | Trp | Leu | Leu | Val | Asn | Pro | Ser | Lys | Val | Tyr | Ser | Glu |
| | | 195 | | | | | 200 | | | | | 205 | | | |

| Lys | Asn | Val | Tyr | Ile | Gln | Asp | Glu | Ile | Gln | Gly | Gly | Gln | Thr | Leu | Glu |
| | 210 | | | | | 215 | | | | | 220 | | | | |

| Pro | Asp | Ser | Phe | Glu | Ile | Val | Val | Thr | Trp | Tyr | Asp | Gly | Tyr | Val | Glu |
| 225 | | | | | 230 | | | | | 235 | | | | | 240 |

| Lys | Phe | Lys | Gly | Lys | Glu | Ala | Ile | Arg | Glu | Phe | His | Asn | Lys | Tyr | Pro |
| | | | | 245 | | | | | 250 | | | | | 255 | |

| Asn | Ser | Asn | Ile | Ser | Val | Ser | Glu | Asn | Lys | Ile | Thr | Val | Asn | Ile | Ser |
| | | | 260 | | | | | 265 | | | | | 270 | | |

| Gln | Glu | Asp | Ser | Thr | Gln | Lys | Phe | Ile | Asn | Ile | Phe | Tyr | Lys | Thr | Lys |
| | | 275 | | | | | 280 | | | | | 285 | | | |

| Ile | Thr | Asn | Pro | Lys | Gln | Lys | Glu | Phe | Val | Asn | Asn | Thr | Lys | Ala | Trp |
| | 290 | | | | | 295 | | | | | 300 | | | | |

| Phe | Lys | Glu | Tyr | Asn | Lys | Pro | Ala | Val | Asn | Gly | Glu | Ser | Phe | Asn | His |
| 305 | | | | | 310 | | | | | 315 | | | | | 320 |

| Ser | Val | Gln | Asn | Ile | Asn | Ala | Asp | Ala | Gly | Val | Asn | Gly | Thr | Val | Lys |
| | | | | 325 | | | | | 330 | | | | | 335 | |

| Gly | Glu | Leu | Lys | Ile | Ile | Lys | Thr | Leu | Lys | Asp | Lys | Ser | Ile | Pro | Ile |
| | | | 340 | | | | | 345 | | | | | 350 | | |

| Lys | Asp | Val | Gln | Phe | Lys | Met | Arg | Arg | Val | Asp | Asn | Thr | Val | Ile | Lys |
| | | 355 | | | | | 360 | | | | | 365 | | | |

Asp Gly Lys Lys Glu Leu Leu Leu Thr Thr Asp Asp Lys Gly Ile Ala
        370                 375                 380

Asn Val Lys Gly Leu Pro Val Gly Lys Tyr Glu Val Lys Glu Ile Ser
385                 390                 395                 400

Ala Pro Glu Trp Ile Ala Phe Asn Pro Leu Ile Ala Pro Lys Leu Glu
                405                 410                 415

Phe Thr Ile Ser Asp Gln Asp Thr Glu Gly Lys Leu Trp Ala Val Glu
                420                 425                 430

Asn Glu Leu Lys Thr Ile Ser Ile Pro Val Glu Lys Val Trp Val Gly
            435                 440                 445

Gln Thr Ser Glu Arg Ala Glu Ile Lys Leu Phe Ala Asp Gly Ile Glu
    450                 455                 460

Val Asp Lys Val Ile Leu Asn Ala Asp Asn Trp Lys His Thr Phe
465                 470                 475                 480

Glu Asn Lys Pro Glu Tyr Asn Ser Glu Thr Lys Gln Lys Ile Asn Tyr
                485                 490                 495

Ser Val Ser Glu Thr Thr Ile Ser Gly Tyr Glu Ser Asn Ile Thr Gly
                500                 505                 510

Asp Ala Lys Asn Gly Phe Ile Val Thr Asn Thr Glu Leu Pro Asp Leu
            515                 520                 525

Thr Ile Gly Lys Glu Val Ile Gly Glu Leu Gly Asp Lys Thr Lys Val
    530                 535                 540

Phe Asn Phe Glu Leu Thr Leu Lys Gln Ala Asp Gly Lys Pro Ile Asn
545                 550                 555                 560

Gly Lys Phe Asn Tyr Ile Gly Ser Val Asp Asp Arg Tyr Lys Lys Glu
                565                 570                 575

Ser Ile Lys Pro Ser Asp Gly Glu Ile Thr Phe Ile Glu Gly Lys Ala
                580                 585                 590

Thr Ile Thr Leu Ser His Gly Gln Glu Ile Thr Ile Lys Asp Leu Pro
            595                 600                 605

Tyr Gly Val Thr Tyr Lys Val Met Glu Lys Glu Ala Asn Glu Asn Gly
    610                 615                 620

Tyr Leu Thr Thr Tyr Asn Gly Asn Asn Glu Val Thr Thr Gly Glu Leu
625                 630                 635                 640

Lys Gln Asp Thr Lys Val Gln Val Val Asn Asn Lys Glu Phe Val Pro
                645                 650                 655

Thr Thr Gly Ile Ser Thr Thr Thr Glu Gln Gly Thr Met Val Gly Met
                660                 665                 670

Val Ile Phe Ser Ile Gly Ile Leu Met Val Met Ile Val Leu Leu
            675                 680                 685

Gln Leu Asn Lys Gly Leu Lys Arg
    690                 695

<210> SEQ ID NO 11
<211> LENGTH: 357
<212> TYPE: PRT
<213> ORGANISM: Clostridium perfringens

<400> SEQUENCE: 11

Met Ile Asn Lys Lys Lys Leu Ser Ala Leu Leu Leu Ser Gly Ala Met
1               5                   10                  15

Phe Met Ser Met Asn Thr Asn Val Phe Ala Ser Asn Leu Pro Ser Gly
                20                  25                  30

Gly Val Glu Gly Thr Glu Gln Asn Pro Ala Lys Ala Thr Ile Thr Lys

```
                35                  40                  45
Asn Phe Glu Phe Pro Glu Gly Ile Asn Thr Pro Ser Ala Thr Phe Lys
         50                  55                  60

Phe Thr Ala Glu Lys Ile Thr Asn Asp Ala Pro Asp Ala Thr Ile Gly
 65                  70                  75                  80

Asp Ile Asn Tyr Thr Gln Gly Asp Asn Gly Thr Leu Ser Asn Gly Lys
                 85                  90                  95

Tyr Ser Val Lys Lys Thr Thr Glu Ile Thr Phe Gly Asn Phe Pro His
                100                 105                 110

Ala Gly Glu Tyr Asp Tyr Asn Val Lys Glu Thr Asn Glu Gly Val Gly
            115                 120                 125

Gly Ile Thr Tyr Asp Thr Lys Glu Tyr Lys Val His Val Tyr Val Ala
            130                 135                 140

Asn Ser Asn Ala Met Asp Gly Lys Thr Tyr Val Lys Ala Ile Thr Ser
145                 150                 155                 160

Glu Asn Gly Gly Glu Lys Ala Pro Ile Glu Phe Val Asn Thr Tyr Lys
                165                 170                 175

Lys Asp Thr Ser Leu Leu Ile Glu Lys Asn Val Ile Gly Asp Leu Ala
            180                 185                 190

Asp Leu Thr Lys Gln Phe Glu Phe Gln Ile Asn Leu Lys Lys Ser Ala
            195                 200                 205

Thr Ser Asp Ile Thr Lys Phe Glu Gly Asn Ile Ile Arg Lys Asp Gly
210                 215                 220

Lys Ile Glu Pro Val Thr Tyr Thr Ala Glu Asn Thr Glu Thr Phe Lys
225                 230                 235                 240

Leu Ala Asn Gly Asp Lys Leu Lys Phe Glu Ser Ile Pro Ala Gly Thr
                245                 250                 255

Lys Tyr Glu Val Lys Glu Ile Gly Ala Ser Asp Gly Tyr Thr Pro Ser
            260                 265                 270

Ile Thr Val Ile Glu Asn Gly Asn Glu Thr Ser Asn Asn Arg Thr Val
            275                 280                 285

Ala Glu Lys Asp Gly Ile Ser Ser Lys Ser Asn Ser Asn Asp Asn Leu
290                 295                 300

Ile Gly Glu Gly Glu Asn Lys Val Thr Phe Thr Asn Thr Tyr Asn Asp
305                 310                 315                 320

Lys Pro Ile Thr Gly Ile Val Met Asn Asn Ile Pro Phe Ile Leu Met
                325                 330                 335

Ile Ser Phe Ala Val Leu Gly Phe Gly Ala Leu Ala Ile Ile Lys Arg
            340                 345                 350

Arg Lys Thr Ile Arg
            355

<210> SEQ ID NO 12
<211> LENGTH: 219
<212> TYPE: PRT
<213> ORGANISM: Clostridium perfringens

<400> SEQUENCE: 12

Met Glu Thr Lys Lys Ile Arg Asn Lys Ile Leu Met Ala Ile Val Ala
 1               5                  10                  15

Leu Ser Phe Ile Leu Leu Pro Asn Thr Arg Val Tyr Ala Thr Glu Asn
                20                  25                  30

Thr Ala Asn Ile Pro Leu Ile Val Arg Gln Glu Phe Asn Val Tyr Thr
            35                  40                  45
```

```
Lys Asp Ser Lys Ala Ile Asp Met Ile Gly Lys Tyr Glu Leu Lys Ala
 50                  55                  60

Ile Ser Glu Asn Ala Pro Met Pro Glu Ser Lys Asn Gly Ser Phe
 65                  70                  75                  80

Ile Phe Asn Ile Asp Gly Asn Asp Lys Gln Phe Thr Ile Pro Leu Ala
                 85                  90                  95

Tyr Thr His Gly Gly Val Tyr Ile Tyr Gln Ile Gln Gln Ile Thr Gln
                100                 105                 110

Ser Lys Asp Asn Tyr Ile Tyr Asp Lys Asn Ser Tyr Lys Ile Thr Val
                115                 120                 125

Tyr Val Lys Asn Ala Glu Asn His Leu Ile Pro Gln Ile Ile Val
 130                 135                 140

Lys Asn Glu Asn Glu Lys Cys Glu Glu Ile Cys Phe Tyr Asn Ile
 145                 150                 155                 160

Tyr Lys Gln Lys Asn Lys Ile Asn Glu Ile Ser Lys Thr Pro Tyr Lys
                165                 170                 175

Pro Asn Gly Ile Asn Val Pro Lys Thr Gly Asp Thr Thr Asn Ile Gly
                180                 185                 190

Phe Tyr Ile Val Ile Leu Ile Ile Ser Leu Gly Leu Leu Val Val Leu
                195                 200                 205

Lys Trp Lys Glu Tyr Lys Lys Arg Lys Lys Glu
 210                 215

<210> SEQ ID NO 13
<211> LENGTH: 680
<212> TYPE: PRT
<213> ORGANISM: Artificial Sequence
<220> FEATURE:
<223> OTHER INFORMATION: cnaA expressed His-tagged

<400> SEQUENCE: 13

Met Gly Ser Ser His His His His His His Ser Ser Gly Leu Val Pro
 1               5                  10                  15

Arg Gly Ser His Met Ala Ser Met Thr Gly Gly Gln Gln Met Gly Arg
                 20                  25                  30

Gly Ser Glu Phe Ser Ser Ile Gln Arg Gly Arg Asp Ile Ser Asn Glu
                 35                  40                  45

Val Val Thr Ser Leu Val Ala Thr Pro Asn Ser Ile Asn Asp Gly Gly
 50                  55                  60

Asn Val Gln Val Arg Leu Glu Phe Lys Glu Asn His Gln Arg Asn Ile
 65                  70                  75                  80

Gln Ser Gly Asp Thr Ile Thr Val Lys Trp Thr Asn Ser Gly Glu Val
                 85                  90                  95

Phe Phe Glu Gly Tyr Glu Lys Thr Ile Pro Leu Tyr Ile Lys Asp Gln
                100                 105                 110

Asn Val Gly Gln Ala Val Ile Glu Lys Thr Gly Ala Thr Leu Thr Phe
                115                 120                 125

Asn Asp Lys Ile Asp Lys Leu Asp Asp Val Gly Gly Trp Ala Thr Phe
 130                 135                 140

Thr Leu Gln Gly Arg Asn Ile Thr Ser Gly Asn His Glu His Thr Gly
 145                 150                 155                 160

Ile Ala Tyr Ile Ile Ser Gly Ser Lys Arg Ala Asp Val Asn Ile Thr
                165                 170                 175

Lys Pro Glu Ser Gly Thr Thr Ser Val Phe Tyr Tyr Lys Thr Gly Ser
                180                 185                 190
```

-continued

```
Met Tyr Thr Asn Asp Thr Asn His Val Asn Trp Trp Leu Val Asn
            195                 200                 205
Pro Ser Lys Val Tyr Ser Glu Lys Asn Val Tyr Ile Gln Asp Glu Ile
210                 215                 220
Gln Gly Gly Gln Thr Leu Glu Pro Asp Ser Phe Glu Ile Val Val Thr
225                 230                 235                 240
Trp Tyr Asp Gly Tyr Val Glu Lys Phe Lys Gly Lys Glu Ala Ile Arg
                245                 250                 255
Glu Phe His Asn Lys Tyr Pro Asn Ser Asn Ile Ser Val Ser Glu Asn
            260                 265                 270
Lys Ile Thr Val Asn Ile Ser Gln Glu Asp Ser Thr Gln Lys Phe Ile
        275                 280                 285
Asn Ile Phe Tyr Lys Thr Lys Ile Thr Asn Pro Lys Gln Lys Glu Phe
    290                 295                 300
Val Asn Asn Thr Lys Ala Trp Phe Lys Glu Tyr Asn Lys Pro Ala Val
305                 310                 315                 320
Asn Gly Glu Ser Phe Asn His Ser Val Gln Asn Ile Asn Ala Asp Ala
                325                 330                 335
Gly Val Asn Gly Thr Val Lys Gly Glu Leu Lys Ile Ile Lys Thr Leu
            340                 345                 350
Lys Asp Lys Ser Ile Pro Ile Lys Asp Val Gln Phe Lys Met Arg Arg
        355                 360                 365
Val Asp Asn Thr Val Ile Lys Asp Gly Lys Lys Glu Leu Leu Leu Thr
    370                 375                 380
Thr Asp Asp Lys Gly Ile Ala Asn Val Lys Gly Leu Pro Val Gly Lys
385                 390                 395                 400
Tyr Glu Val Lys Glu Ile Ser Ala Pro Glu Trp Ile Ala Phe Asn Pro
                405                 410                 415
Leu Ile Ala Pro Lys Leu Glu Phe Thr Ile Ser Asp Gln Asp Thr Glu
            420                 425                 430
Gly Lys Leu Trp Ala Val Glu Asn Glu Leu Lys Thr Ile Ser Ile Pro
        435                 440                 445
Val Glu Lys Val Trp Val Gly Gln Thr Ser Glu Arg Ala Glu Ile Lys
    450                 455                 460
Leu Phe Ala Asp Gly Ile Glu Val Asp Lys Val Ile Leu Asn Ala Asp
465                 470                 475                 480
Asn Asn Trp Lys His Thr Phe Glu Asn Lys Pro Glu Tyr Asn Ser Glu
                485                 490                 495
Thr Lys Gln Lys Ile Asn Tyr Ser Val Ser Glu Thr Thr Ile Ser Gly
            500                 505                 510
Tyr Glu Ser Asn Ile Thr Gly Asp Ala Lys Asn Gly Phe Ile Val Thr
        515                 520                 525
Asn Thr Glu Leu Pro Asp Leu Thr Ile Gly Lys Glu Val Ile Gly Glu
    530                 535                 540
Leu Gly Asp Lys Thr Lys Val Phe Asn Phe Glu Leu Thr Leu Lys Gln
545                 550                 555                 560
Ala Asp Gly Lys Pro Ile Asn Gly Lys Phe Asn Tyr Ile Gly Ser Val
                565                 570                 575
Asp Asp Arg Tyr Lys Lys Glu Ser Ile Lys Pro Ser Asp Gly Glu Ile
            580                 585                 590
Thr Phe Ile Glu Gly Lys Ala Thr Ile Thr Leu Ser His Gly Gln Glu
        595                 600                 605
Ile Thr Ile Lys Asp Leu Pro Tyr Gly Val Thr Tyr Lys Val Met Glu
```

```
              610                 615                 620
Lys Glu Ala Asn Glu Asn Gly Tyr Leu Thr Thr Tyr Asn Gly Asn Asn
625                 630                 635                 640

Glu Val Thr Thr Gly Glu Leu Lys Gln Asp Thr Lys Val Gln Val Val
                645                 650                 655

Asn Asn Lys Glu Phe Val Pro Thr Thr Val Asp Lys Leu Ala Ala Ala
                660                 665                 670

Leu Glu His His His His His His
                675                 680

<210> SEQ ID NO 14
<211> LENGTH: 349
<212> TYPE: PRT
<213> ORGANISM: Artificial Sequence
<220> FEATURE:
<223> OTHER INFORMATION: fimA expressed His-tagged

<400> SEQUENCE: 14

Met Gly Ser Ser His His His His His Ser Ser Gly Leu Val Pro
1               5                   10                  15

Arg Gly Ser His Met Ala Ser Met Thr Gly Gly Gln Gln Met Gly Arg
                20                  25                  30

Gly Ser Glu Phe Ser Asn Leu Pro Ser Gly Gly Val Glu Gly Thr Glu
            35                  40                  45

Gln Asn Pro Ala Lys Ala Thr Ile Thr Lys Asn Phe Glu Phe Pro Glu
        50                  55                  60

Gly Ile Asn Thr Pro Ser Ala Thr Phe Lys Phe Thr Ala Glu Lys Ile
65                  70                  75                  80

Thr Asn Asp Ala Pro Asp Ala Thr Ile Gly Asp Ile Asn Tyr Thr Gln
                85                  90                  95

Gly Asp Asn Gly Thr Leu Ser Asn Gly Lys Tyr Ser Val Lys Lys Thr
            100                 105                 110

Thr Glu Ile Thr Phe Gly Asn Phe Pro His Ala Gly Glu Tyr Asp Tyr
        115                 120                 125

Asn Val Lys Glu Thr Asn Glu Gly Val Gly Gly Ile Thr Tyr Asp Thr
    130                 135                 140

Lys Glu Tyr Lys Val His Val Tyr Val Ala Asn Ser Asn Ala Met Asp
145                 150                 155                 160

Gly Lys Thr Tyr Val Lys Ala Ile Thr Ser Glu Asn Gly Gly Glu Lys
                165                 170                 175

Ala Pro Ile Glu Phe Val Asn Thr Tyr Lys Lys Asp Thr Ser Leu Leu
            180                 185                 190

Ile Glu Lys Asn Val Ile Gly Asp Leu Ala Asp Leu Thr Lys Gln Phe
        195                 200                 205

Glu Phe Gln Ile Asn Leu Lys Lys Ser Ala Thr Ser Asp Ile Thr Lys
    210                 215                 220

Phe Glu Gly Asn Ile Ile Arg Lys Asp Gly Lys Ile Glu Pro Val Thr
225                 230                 235                 240

Tyr Thr Ala Glu Asn Thr Glu Thr Phe Lys Leu Ala Asn Gly Asp Lys
                245                 250                 255

Leu Lys Phe Glu Ser Ile Pro Ala Gly Thr Lys Tyr Glu Val Lys Glu
            260                 265                 270

Ile Gly Ala Ser Asp Gly Tyr Thr Pro Ser Ile Thr Val Ile Glu Asn
        275                 280                 285

Gly Asn Glu Thr Ser Asn Asn Arg Thr Val Ala Glu Lys Asp Gly Ile
```

```
                290                 295                 300
Ser Ser Lys Ser Asn Ser Asn Asp Asn Leu Ile Gly Glu Gly Glu Asn
305                 310                 315                 320

Lys Val Thr Phe Thr Asn Thr Tyr Asn Asp Lys Pro Ile Thr Val Asp
                325                 330                 335

Lys Leu Ala Ala Ala Leu Glu His His His His His His
                340                 345

<210> SEQ ID NO 15
<211> LENGTH: 207
<212> TYPE: PRT
<213> ORGANISM: Artificial Sequence
<220> FEATURE:
<223> OTHER INFORMATION: fimB expressed His-tagged

<400> SEQUENCE: 15

Met Gly Ser Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Thr Glu Asn Thr Ala Asn Ile Pro Leu Ile Val Arg
        35                  40                  45

Gln Glu Phe Asn Val Tyr Thr Lys Asp Ser Lys Ala Ile Asp Met Ile
    50                  55                  60

Gly Lys Tyr Glu Leu Lys Ala Ile Ser Glu Asn Ala Pro Met Pro Glu
65                  70                  75                  80

Glu Ser Lys Asn Gly Ser Phe Ile Phe Asn Ile Asp Gly Asn Asp Lys
                85                  90                  95

Gln Phe Thr Ile Pro Leu Ala Tyr Thr His Gly Gly Val Tyr Ile Tyr
            100                 105                 110

Gln Ile Gln Gln Ile Thr Gln Ser Lys Asp Asn Tyr Ile Tyr Asp Lys
        115                 120                 125

Asn Ser Tyr Lys Ile Thr Val Tyr Val Lys Asn Ala Glu Asn Asn His
    130                 135                 140

Leu Ile Pro Gln Ile Ile Val Lys Asn Glu Asn Asn Glu Lys Cys Glu
145                 150                 155                 160

Glu Ile Cys Phe Tyr Asn Ile Tyr Lys Gln Lys Asn Lys Ile Asn Glu
                165                 170                 175

Ile Ser Lys Thr Pro Tyr Lys Pro Asn Gly Ile Asn Val Pro Lys Thr
            180                 185                 190

Val Asp Lys Leu Ala Ala Ala Leu Glu His His His His His
        195                 200                 205

<210> SEQ ID NO 16
<211> LENGTH: 5
<212> TYPE: PRT
<213> ORGANISM: Artificial Sequence
<220> FEATURE:
<223> OTHER INFORMATION: LPXTG motif
<220> FEATURE:
<221> NAME/KEY: MISC_FEATURE
<222> LOCATION: (3)..(3)
<223> OTHER INFORMATION: any amino acid

<400> SEQUENCE: 16

Leu Pro Xaa Thr Gly
1               5
```

VACCINE AGAINST NECROTIC ENTERITIS IN POULTRY

CROSS REFERENCE TO RELATED APPLICATIONS

This application is a National Stage of International Application No. PCT/CA2018/050643, filed on May 31, 2018; which claims the benefit of U.S. Provisional Application Ser. No. 62/513,001, filed May 31, 2017, both of which are hereby incorporated by reference in their entirety.

The Sequence Listing for this application is labeled "SeqList-07Apr21-ST25.txt", which was created on Apr. 7, 2021, and is 38 KB. The entire content is incorporated herein by reference in its entirety.

BACKGROUND

The present application is directed to polypeptides useful in preparing a vaccine against necrotic enteritis in poultry. More specifically, the present application is directed to a *Clostridium perfringens* pilus polypeptide useful in preparing a vaccine against necrotic enteritis related to *Clostridium perfringens* infection in poultry.

Necrotic enteritis is an intestinal disease of poultry such as broiler chickens, that in 2015 was estimated to cost the poultry industry $US 6 billion in losses. Necrotic enteritis is caused primarily by certain Type A strains of *Clostridium perfringens* that produce the NetB pore-forming toxin, which overgrow and adhere to the intestinal mucosa, eventually causing the characteristic lesions of the disease. *Clostridium perfringens* is a normal inhabitant of the intestinal tract, and typically only those strains that carry the NetB toxin can cause necrotic enteritis. Necrotic enteritis is primarily controlled by application of in-feed antibiotics, a practice that is increasingly discouraged due to the potential spread of antimicrobial resistance, and which is currently being phased out of production in some countries. It is therefore important, from both a financial and public health perspective, to find alternative approaches to control necrotic enteritis, such as the development of a vaccine.

A *Clostridium perfringens* adherence genetic locus (VR-10B) has been recently identified through its association with NetB-positive strains (Lepp D, Gong J, Songer J G, Boerlin P, Parreira V R, Prescott J F. 2013. Identification of Accessory Genome Regions in Poultry *Clostridium perfringens* Isolates Carrying the netB Plasmid. Journal of Bacteriology 195: 1152-1166). The identified genetic locus was found to be present in 87% of netB-positive and 42% of netB-negative isolates, of 54 poultry isolates examined. This genetic locus (subsequently renamed the collagen adhesion (CA) locus) was later shown to be involved in collagen binding, and required for necrotic enteritis pathogenesis (Wade B, Keyburn A L, Haring V, Ford M, Rood J I, Moore R J: The adherent abilities of *Clostridium perfringens* strains are critical for the pathogenesis of avian necrotic enteritis. Vet Microbiol 2016, 197: 53-61; Wade B, Keyburn A L, Seemann T, Rood J I, Moore R J: Binding of *Clostridium perfringens* to collagen correlates with the ability to cause necrotic enteritis in chickens. Vet Microbiol 2015, 180: 299-303.).

A number of *Clostridium perfringens* proteins have previously been evaluated as vaccine candidates. However, these proteins offer at best partial protection against necrotic enteritis. In addition, many of these proteins are not specific to necrotic enteritis-causing strains, and are not known to play a role in necrotic enteritis pathogenesis. Therefore, it is desirable to identify alternative *Clostridium perfringens* polypeptides which may be candidates for producing a vaccine against necrotic enteritis.

SUMMARY

One aspect of the present invention provides an isolated *Clostridium perfringens* pilus polypeptide. In another aspect, the present invention provides an immunogenic polypeptide selected from an isolated *Clostridium perfringens* pilus polypeptide, a variant of the pilus polypeptide; a fragment of the pilus polypeptide; and a fragment of the variant, wherein the pilus polypeptide, the variant, the fragment of the polypeptide and the fragment of the variant are immunogenic in poultry. In at least one embodiment, the pilus polypeptide is a CnaA polypeptide. In at least one embodiment, the pilus polypeptide is a FimA polypeptide. In at least one embodiment, the pilus polypeptide is a FimB polypeptide. In at least one embodiment, the pilus polypeptide is an assembled pilus.

Another aspect of the present invention provides a polynucleotide comprising a sequence encoding an isolated *Clostridium perfringens* pilus polypeptide or an immunogenic polypeptide as described herein. In another aspect, the present application provides a vector comprising a polynucleotide having a sequence encoding an isolated *Clostridium perfringens* pilus polypeptide or an immunogenic polypeptide as described herein, wherein the vector is configured for expression of the isolated *Clostridium perfringens* pilus polypeptide or immunogenic polypeptide in a host cell.

In another aspect, the present invention provides a vaccine for the treatment or prevention of necrotic enteritis in poultry, wherein the vaccine comprises an immunogenic polypeptide as described herein. In another aspect, the present application provides a vaccine for the treatment or prevention of *Clostridium perfringens* infection in poultry, wherein the vaccine comprises an immunogenic polypeptide as described herein.

In another aspect, the present invention provides the use of an immunogenic polypeptide as described herein in the preparation of a medicament for the treatment or prevention of necrotic enteritis in poultry or for the treatment or prevention of *Clostridium perfringens* infection in poultry.

In another aspect, the present invention provides a method of treatment or prevention of necrotic enteritis in poultry or for the treatment or prevention of *Clostridium perfringens* infection in poultry, the method comprising administering an effective amount of an immunogenic polypeptide as described herein, or a vaccine thereof, to the poultry.

In another aspect, the present invention provides the use of an immunogenic polypeptide as described herein as a vaccine for the treatment or prevention of necrotic enteritis in poultry or for the treatment or prevention of *Clostridium perfringens* infection in poultry.

A further aspect of the present invention provides an antibody which binds selectively to an immunogenic polypeptide as described herein. In another aspect, the present invention provides a method of detecting *Clostridium perfringens* infection in poultry by obtaining a biological sample from the poultry and detecting in the biological sample the presence of an antibody which binds selectively to an immunogenic polypeptide as described herein. Yet another aspect of the present invention provides a method of detecting an immunogenic polypeptide as described herein comprising exposing the immunogenic polypeptide to an antibody which binds selectively to the immunogenic polypeptide and detecting binding of the immunogenic polypeptide to the antibody.

BRIEF DESCRIPTION OF THE DRAWINGS

Further features of the present invention will become apparent from the following written description and the accompanying figures, in which:

FIG. 8A is a photograph illustrating separation by SDS-PAGE of surface polypeptides extracted from *Clostridium perfringens* strain CP1 or CP1 null mutants of genes for each of the pilus subunits cnaA, fimA and fimB (CP1ΔcnaA, CP1ΔfimA, and CP1ΔfimB), visualized with COOMASSIE stain;

FIG. 8B is a photograph illustrating a Western blot analysis of SDS-PAGE-separated surface polypeptides extracted from *Clostridium perfringens* strain CP1 or CP1 null mutants of genes for each of the pilus subunits cnaA, fimA and fimB (CP1ΔcnaA, CP1ΔfimA, and CP1ΔfimB), detected using anti-FimA antibodies obtained from chicken serum as the primary antibody;

FIG. 8C is a photograph illustrating a Western blot analysis of SDS-PAGE-separated surface polypeptides extracted from *Clostridium perfringens* strain CP1 or CP1 null mutants of genes for each of the pilus subunits cnaA, fimA and fimB (CP1ΔcnaA, CP1ΔfimA, and CP1ΔfimB), detected using anti-FimA antibodies raised in rabbits as the primary antibody;

FIG. 9A is a photograph illustrating separation by SDS-PAGE of surface polypeptides extracted from various *Clostridium perfringens* strains visualized with COOMASSIE stain;

FIG. 9B is a photograph illustrating a Western blot analysis of SDS-PAGE-separated surface polypeptides extracted from various *Clostridium perfringens* strains visualized with anti-FimA antibodies obtained from chicken serum as the primary antibody; and FIG. 10 is a series of photographs obtained by transmission electron microscopy of cells of *Clostridium perfringens* strain CP1 or of the CP1 null mutants CP1ΔfimA, and CP1ΔfimB labeled with gold particles using rabbit anti-FimA antibody as a primary antibody and 6 nm immuno-gold-labelled goat anti-rabbit IgG as a secondary antibody.

DETAILED DESCRIPTION

Figure 1:
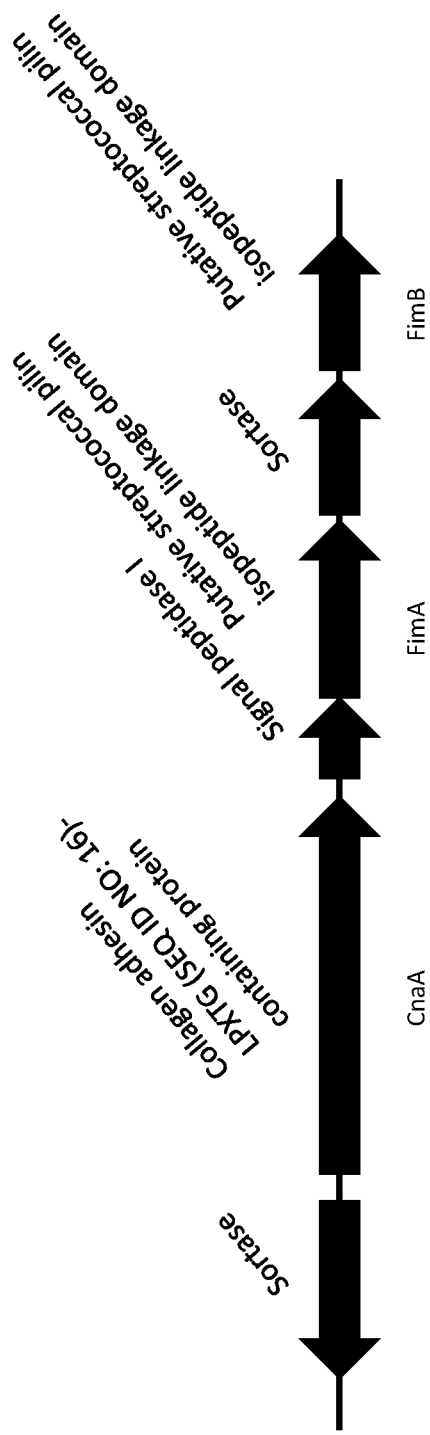
FIG. 1 is a diagrammatic representation of the 5.2 kilobase-pair *Clostridium perfringens* VR-10B chromosomal locus.
Figure 2A:
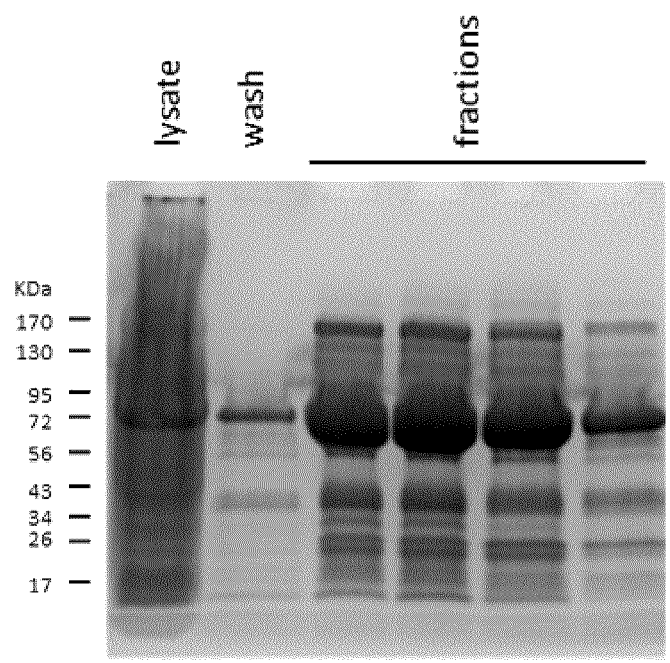
FIG. 2A is a photograph illustrating separation of recombinant histidine-tagged pilus subunit polypeptide CnaA by sodium dodecyl sulfate-polyacrylamide gel electrophoresis (SDS-PAGE) visualized by COOMASSIE staining.
Figure 2B:
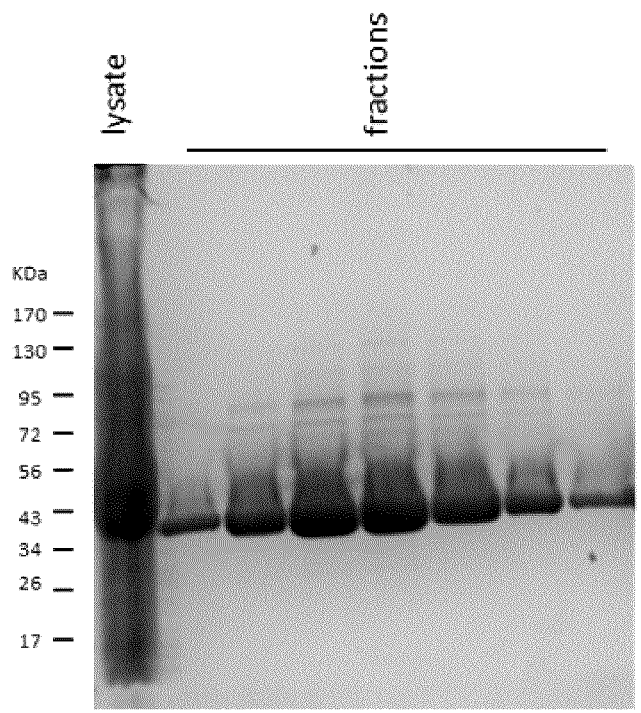
FIG. 2B is a photograph illustrating separation of recombinant pilus subunit polypeptide FimA by SDS-PAGE visualized by COOMASSIE staining.
Figure 2C:
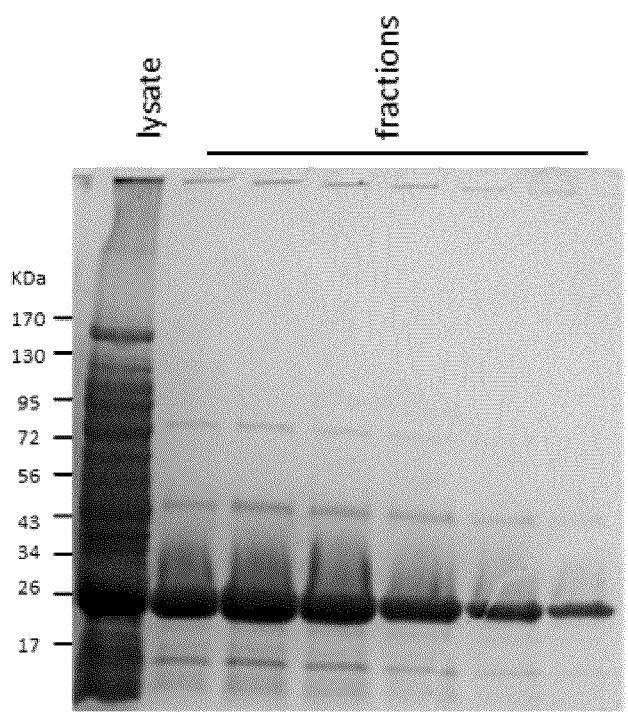
FIG. 2C is a photograph illustrating separation of recombinant pilus subunit polypeptide FimB by SDS-PAGE visualized by COOMASSIE staining.
Figure 2D:
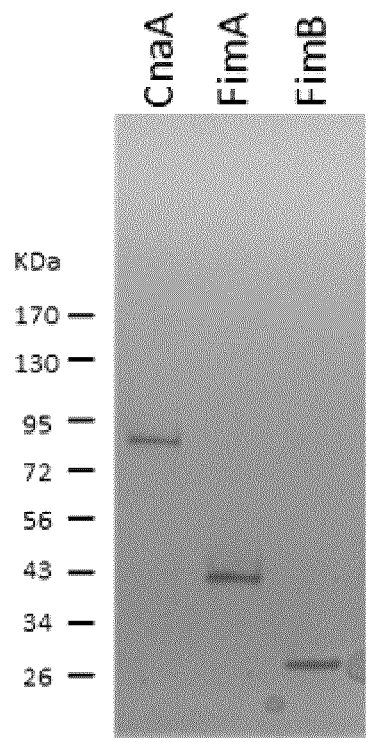
FIG. 2D is a photograph illustrating visualization by SDS-PAGE and COOMASSIE staining of pooled fractions of CnaA, FimA and FimB following concentration and desalting.

It has been found by the present applicants that the VR-10B genetic locus identified in strains of *Clostridium perfringens* associated with necrotic enteritis in poultry (Lepp D et al, *Journal of Bacteriology* (2013) 195: 1152-1166) contains six putative genes which have been found to encode an adhesive pilus: three genes (cnaA, fimA and fimB) encoding structural pilus subunits, and genes encoding two sortases and a signal peptidase presumably involved in pilus assembly. A diagrammatic representation of the VR-10B locus is shown in FIG. 1.

A pilus is a hair-like structure that is present on the surface of many bacteria and is often involved in virulence. This type of pilus is composed of covalently-linked major and minor polypeptide subunits that form a cell surface structure having a length of approximately 1 μm. Pili have been extensively studied in Gram-negative bacteria, but several Gram-positive species, including *Corynebacterium diphtheriae, Streptococcus pneumoniae,* and *Streptococcus pyogenes*, have more recently been shown to produce a specific type of pilus that is assembled by sortase enzymes. This type of adhesive Gram-positive pilus is assembled at the cell surface via covalent linkage of pilin subunits by housekeeping and pilin-specific sortase enzymes, and is eventually covalently linked to the cell wall peptidoglycan to form the assembled pilus.

Without being bound by theory, it is contemplated that the *Clostridium perfringens* pilus polypeptides described herein may be a viable and promising target for development of a vaccine against necrotic enteritis for a number of reasons. The gene locus is present mainly in necrotic enteritis-causing strains of *Clostridium perfringens*. Therefore, the immune response elicited by an immunogenic pilus protein is expected to specifically target strains of *Clostridium perfringens* that cause disease. In addition, pili are present on the surface of the bacterial cell, and are often involved in attachment to the host during the pathogenesis of bacterial infections, which can expose the pili to the host immune system. Furthermore, possibly because of their role in disease and their location on the bacterial cell surface, pili have been successfully used to develop vaccines for a number of other infectious diseases.

Thus, one aspect of the present application provides an immunogenic polypeptide selected from an isolated *Clostridium perfringens* pilus polypeptide, a variant of the pilus polypeptide; a fragment of the pilus polypeptide; and a fragment of the variant, wherein the pilus polypeptide, the variant, the fragment of the polypeptide and the fragment of the variant are immunogenic in poultry.

As used herein, the term "poultry" is used to refer to species of birds or fowl which are raised agriculturally for products including but not limited to meat, eggs and feathers. Poultry include but are not limited to chickens, turkeys, ducks, geese, quail, ostriches, pheasants and other agriculturally relevant birds or fowl. Especially included are poultry which are susceptible to necrotic enteritis caused by *Clostridium perfringens* infection. In at least one embodiment, the poultry are broilers or chickens raised for meat production.

As used herein, the term "polypeptide" is intended to mean a compound containing two or more amino acid residues linked together by peptide bonds. Polypeptides include but are not limited to oligopeptides or polypeptides in which two or more amino acid residues are linked together sequentially by covalent peptide bonds to form a single polypeptide strand, and proteins comprising two or more polypeptide strands non-covalently associated with each other or linked with each other by covalent bonds other than peptide bonds, including but not limited to disulfide bonds and isopeptide bonds. As used herein, the term "isopeptide bond" is intended to mean an amide bond formed between an amino group of one amino acid and a carboxyl group of a second amino acid, wherein at least one of the amino group and the carboxyl group is located on the side chain of the respective amino acid.

As used herein, the term "*Clostridium perfringens* pilus polypeptide" is intended to mean a polypeptide which has the function of a pilus or a pilus subunit and which is encoded by one or more genes found in a strain of *Clostridium perfringens* associated with necrotic enteritis in poultry. In at least one embodiment, the gene is the cnaA gene, the fimA gene, or the fimB gene found in the VR-10B genetic locus identified in Lepp D et al, *Journal of Bacteriology* (2013) 195: 1152-1166, as diagrammatically represented in FIG. 1.

As used herein, the term "variant" when used in reference to a polypeptide is intended to refer to a polypeptide which differs in its amino acid sequence from the sequence of a reference polypeptide to which the variant is being compared by one or more amino acid residues. The differences between the sequence of the variant and the sequence of the reference polypeptide can include substitution of one or more amino acid residues with different amino acid residues, insertion of additional amino acid residues or deletion of amino acid residues. In certain embodiments, a variant can differ from a reference polypeptide by conservative substitution of one or more amino acid residues with replacement amino acid residues which may have similar properties, including but not limited to charge, size and hydrophilicity, to the amino acid residues which the new residues replace. In certain embodiments, variants may completely or partially retain one or more biological functions of the reference polypeptide, including but not limited to immunogenicity. In at least one embodiment, the reference polypeptide is an isolated *Clostridium perfringens* pilus polypeptide as described herein.

In at least one embodiment, the sequence of a variant can have at least 75%, at least 80%, at least 85%, at least 90%, at least 95%, at least 99% or at least 99.9% identity to the sequence of a reference polypeptide. As used herein, the term "percent identity" or "% identity" when used in reference to the sequence of a polypeptide or a polynucleotide is intended to mean the percentage of the total number of amino acid or nucleotide residues, respectively, in the sequence which are identical to those at the corresponding position of a reference polypeptide or polynucleotide sequence. In at least one embodiment, when the length of the variant sequence and the length of the reference sequence are not identical, percent identity can be calculated based on the total number of residues in the variant sequence or based on the total number or residues in the reference sequence. Percent identity can be measured by various local or global sequence alignment algorithms well known in the art, including but not limited to the Smith-Waterman algorithm and the Needleman-Wunsch algorithm. Tools using these or other suitable algorithms include but are not limited to BLAST (Basic Local Alignment Search Tool) and other such tools well known in the art.

As used herein, the term "fragment" when used in relation to a polypeptide or a variant is intended to refer to a smaller polypeptide containing fewer amino acid residues than the polypeptide or variant and having a sequence which is identical to a portion of the sequence of the polypeptide or variant. In at least one embodiment, the fragment retains one or more biological activities of the polypeptide or variant, including but not limited to immunogenicity. In at least one embodiment, the fragment comprises an epitope of the polypeptide or variant. In at least one embodiment, the fragment is at least 6 amino acids in length or at least 7 amino acids in length, or at least 8 amino acids in length or at least 9 amino acids in length or at least 10 amino acids in length.

As used herein, the term "immunogenic" is intended to refer to an agent, including but not limited to a polypeptide or polynucleotide or a fragment thereof, which is capable of eliciting an immunoprotective response in a subject to which the immunogenic agent is administered. As used herein, the term "immunoprotective response" is intended to refer to an immune response that prevents, reduces or eliminates one or more of the symptoms of disease in an infected subject.

The present immunogenic polypeptide, including the present isolated *Clostridium perfringens* pilus polypeptide, the variant of the pilus polypeptide, the fragment of the pilus polypeptide and the fragment of the variant, are immunogenic in poultry. Thus, in at least one embodiment, poultry immunized with any one or more of the present isolated *Clostridium perfringens* pilus polypeptide, the variant of the pilus polypeptide, the fragment of the pilus polypeptide and the fragment of the variant will show an immunoprotective response to challenge with one or more of a *Clostridium perfringens* cell, an assembled *Clostridium perfringens* pilus, a *Clostridium perfringens* pilus polypeptide, a fragment of a *Clostridium perfringens* pilus polypeptide, or a portion of a *Clostridium perfringens* cell, including but not limited to a cell membrane or portion thereof, or a cell wall or a portion thereof, which bears one or more of an assembled *Clostridium perfringens* pilus, a *Clostridium perfringens* pilus polypeptide or a fragment of a *Clostridium perfringens* pilus polypeptide.

Another aspect of the present application provides a polynucleotide comprising a sequence encoding an isolated *Clostridium perfringens* pilus polypeptide or an immunogenic polypeptide as described herein. In at least one embodiment, the polynucleotide is messenger RNA (mRNA) having a sequence which can be translated to generate the isolated *Clostridium perfringens* pilus polypeptide or the immunogenic polypeptide. In at least one embodiment, the polynucleotide is DNA, at least one strand of which can be transcribed to produce mRNA which in turn can be translated to generate the isolated *Clostridium perfringens* pilus polypeptide or the immunogenic polypeptide. In at least one embodiment, the DNA can be expressed by a biochemical system, including but not limited to a cell, to produce the isolated *Clostridium perfringens* pilus polypeptide or the immunogenic polypeptide. In at least one such embodiment, the DNA can be incorporated into a vector configured for expression of the DNA in a host cell, as well known in the art.

In at least one embodiment, the polynucleotide can include a variant polynucleotide sequence which hybridizes to a polynucleotide comprising a sequence encoding an isolated *Clostridium perfringens* pilus polypeptide or an immunogenic polypeptide as described herein under at least moderately stringent conditions. By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrid, is determined by the melting temperature ($T_m$), which in sodium-containing buffers is a function of the sodium ion concentration ([Na$^+$]) and temperature ($T_m$=81.5° C.−16.6 ($Log_{10}$[Na$^+$])+0.41(% (G+C)−600/l), where % G+C is the percentage of cytosine and guanine nucleotides in the nucleic acid and l is the length of the nucleic acid in base pairs, or similar equation). Accordingly, the parameters in the wash conditions that determine hybrid stability are sodium ion concentration and temperature. In order to identify molecules that are similar, but not identical, to a known nucleic acid molecule, a 1% mismatch may be assumed to result in about a 1° C. decrease in $T_m$. For example, if nucleic acid molecules are sought that have a >95% identity, the final wash temperature may be reduced by about 5° C. Based on these considerations those skilled in the art will be able to readily select appropriate hybridization conditions.

In some embodiments, stringent hybridization conditions are selected. By way of example the following conditions may be employed to achieve stringent hybridization: hybridization at 5× sodium chloride/sodium citrate (SSC)/5×Denhardt's solution/1.0% sodium dodecylsulfate (SDS) at $T_m$−5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 2002, and in: Sambrook et al., Molecular Cloning: a Laboratory Manual, Cold Spring Harbor Laboratory Press, 2001.

In at least one embodiment, the isolated *Clostridium perfringens* pilus polypeptide is a CnaA polypeptide. In at least one embodiment, the CnaA polypeptide has an amino acid sequence selected from SEQ ID NO:10 and SEQ ID NO:13. In at least one embodiment, the CnaA polypeptide is encoded by a polynucleotide having a sequence selected from SEQ ID NO:1, SEQ ID NO:4 and SEQ ID NO:7. In at least one embodiment, the CnaA polypeptide is encoded by a polynucleotide which hybridizes under at least moderately stringent conditions to a polynucleotide having a sequence selected from SEQ ID NO:1, SEQ ID NO:4 and SEQ ID NO:7. In at least one embodiment, when the pilus polypeptide is a CnaA polypeptide, the variant has at least 75%, 80%, 85%, 90%, 95%, 99% or 99.9% sequence identity to an amino acid sequence selected from SEQ ID NO:10 and SEQ ID NO:13.

In at least one embodiment, the isolated *Clostridium perfringens* pilus polypeptide is a FimA polypeptide. In at least one embodiment, the FimA polypeptide has an amino acid sequence selected from SEQ ID NO:11 and SEQ ID NO:14. In at least one embodiment, the FimA polypeptide is encoded by a polynucleotide having a sequence selected from SEQ ID NO:2, SEQ ID NO:5 and SEQ ID NO:8. In at least one embodiment, the FimA polypeptide is encoded by a polynucleotide which hybridizes under at least moderately stringent conditions to a polynucleotide having a sequence selected from SEQ ID NO:2, SEQ ID NO:5 and SEQ ID NO:8. In at least one embodiment, when the pilus polypeptide is a FimA polypeptide, the variant has at least 75%, 80%, 85%, 90%, 95%, 99% or 99.9% sequence identity to an amino acid sequence selected from SEQ ID NO:11 and SEQ ID NO:14.

In at least one embodiment, the isolated *Clostridium perfringens* pilus polypeptide is a FimB polypeptide. In at least one embodiment, the FimB polypeptide has an amino acid sequence selected from SEQ ID NO:12 and SEQ ID NO:15. In at least one embodiment, the FimB polypeptide is encoded by a polynucleotide having a sequence selected from SEQ ID NO:3, SEQ ID NO:6 and SEQ ID NO:9. In at least one embodiment, the FimB polypeptide is encoded by a polynucleotide which hybridizes under at least moderately stringent conditions to a polynucleotide having a sequence selected from SEQ ID NO:3, SEQ ID NO:6 and SEQ ID NO:9. In at least one embodiment, when the pilus polypeptide is a FimB polypeptide, the variant has at least 75%, 80%, 85%, 90%, 95%, 99% or 99.9% sequence identity to an amino acid sequence selected from SEQ ID NO:12 and SEQ ID NO:15.

In at least one embodiment, the isolated *Clostridium perfringens* pilus polypeptide is an assembled pilus. In at least one embodiment, the assembled pilus comprises one or more subunits, each individually selected from a CnaA polypeptide, a FimA polypeptide, and a FimB polypeptide. In at least one embodiment, the one or more subunits are covalently bonded to each other. In at least one embodiment, the assembled pilus is a pilus isolated from a *Clostridium perfringens* cell, or a portion thereof including but not limited to a cell membrane or a portion thereof or a cell wall or a portion thereof. In at least one embodiment, the assembled pilus is a fragment of a pilus isolated from a *Clostridium perfringens* cell, or a portion thereof including but not limited to a cell membrane or a portion thereof or a cell wall or a portion thereof, wherein the fragment comprises one or more subunits, each individually selected from a CnaA polypeptide, a FimA polypeptide, and a FimB polypeptide.

In at least one embodiment, the isolated *Clostridium perfringens* pilus polypeptide can be isolated from a culture of *Clostridium perfringens*. Thus, in at least one embodiment, the isolated *Clostridium perfringens* pilus polypeptide can be part of a preparation containing one or more portions of a *Clostridium perfringens* cell, including but not limited to a cell membrane or a portion thereof or a cell wall or a portion thereof, which bears the pilus polypeptide or a fragment thereof as described herein. In at least one embodiment, the isolated *Clostridium perfringens* pilus polypeptide can be recombinantly produced by expression in a suitable host cell of a vector comprising a polynucleotide having a sequence encoding the pilus polypeptide. In at least one embodiment, when the pilus polypeptide is an assembled pilus, the assembled pilus can be recombinantly produced by expression in a suitable host cell of a vector comprising a polynucleotide having a sequence encoding genes and other nucleotide sequences required for assembly of the assembled pilus. In addition, the isolated *Clostridium perfringens* pilus polypeptide can be at least partially purified after isolation or recombinant production. Suitable vectors and host cells, including but not limited to prokaryotic and eukaryotic host cells adapted for the production of recombinant polypeptides, and methods of isolating or recombinantly producing such polypeptides, including methods of at least partial purification of such polypeptides, are well known in the art or can be readily identified and selected by the skilled person with no more than routine experimental effort.

In another aspect, the present application provides a vaccine for the treatment or prevention of necrotic enteritis in poultry, or for the treatment or prevention of *Clostridium perfringens* infection in poultry, wherein the vaccine comprises at least one immunogenic polypeptide as described herein. As used herein, the term "vaccine" is intended to refer to an immunogenic preparation used to prevent, treat or reduce the effects of infection by *Clostridium perfringens*. Vaccine formulations typically contain an immunologically effective amount of an immunogenic agent, and may also contain an adjuvant or may be adjuvant-free. In the case of the present vaccine, the immunogenic agent can be an immunogenic polypeptide as described herein.

As used herein, the term "adjuvant" is intended to refer to an agent which is effective for enhancing an immune response against an immunogenic agent of a subject vaccinated with a vaccine comprising the immunogenic agent. Suitable adjuvants are well known in the art and include but are not limited to inorganic compounds including but not limited to alum, aluminum hydroxide, and other aluminum-containing compounds; saponins including but not limited to Quil-A™; Freund's complete and incomplete adjuvants; lipid or mineral oil-containing adjuvants, including but not limited to oil-in-water emulsions; polysaccharide adjuvants; protein adjuvants; immunomodulators; adjuvants obtained from killed or attenuated bacterial cells; and other suitable adjuvants known in the art.

Vaccines can be formulated in one or more pharmaceutically acceptable carriers. As used herein, the term "pharmaceutically acceptable" is intended to refer to molecular entities and compositions that are physiologically tolerable and do not typically produce untoward reactions when administered to an animal or a human. Preferably, as used herein, the term "pharmaceutically acceptable" means approved by a regulatory agency of the federal or a state government or listed in the U.S. Pharmacopeia or other generally recognized pharmacopeia for use in animals or humans. As used herein, the term "carrier" is intended to refer to a diluent, adjuvant, excipient, or vehicle with which a compound is administered. Suitable carriers are well known in the art and, in at least one embodiment, are described in "Remington's Pharmaceutical Sciences" by E. W. Martin, 18th Edition, or other editions.

The vaccines can be formulated for administration by any convenient route known in the art, including but not limited to orally, rectally, nasally, transmucosally, transdermally, parenterally, intravenously, intramuscularly, subcutaneously, in ovo, or by other known routes. In at least one embodiment, it is contemplated that the vaccine can be administered orally. Without being bound by theory, it is contemplated that oral vaccination can directly target gut-associated lymphoid tissues, at the site of infection by necrotic enteritis-associated strains of *Clostridium perfringens*. In at least one embodiment, it is contemplated that progeny can be immunized by vaccination of a mother and subsequent transfer of maternal immunity, including but not limited to maternal antibodies, to the progeny.

In another aspect, the present invention provides the use of an immunogenic polypeptide as described herein in the preparation of a medicament for the treatment or prevention of necrotic enteritis in poultry or for the treatment or prevention of *Clostridium perfringens* infection in poultry. The medicament can be a vaccine as described herein.

In another aspect, the present invention provides a method of treatment or prevention of necrotic enteritis in poultry or for the treatment or prevention of *Clostridium perfringens* infection in poultry, the method comprising administering an effective amount of an immunogenic polypeptide or of a vaccine as described herein to the poultry. Administration can be by routes well known in the art, including but not limited to orally, rectally, nasally, parenterally, intravenously, intramuscularly, subcutaneously or by other routes. In at least one embodiment, administration can be by subcutaneous injection. In at least one embodiment, administration can be oral. In at least one embodiment, the vaccine can be administered more than once to the poultry, to provide an initial immunization followed by one or more booster immunizations, as understood in the art. In at least one embodiment, one or more of the initial immunization and the one or more booster immunizations are administered to the poultry after the disappearance of maternal antibodies in the poultry. In at least one such embodiment, one or more of the initial immunization and the one or more booster immunizations are administered to the poultry no earlier than about 10 days after hatching.

In another aspect, the present invention provides the use of an immunogenic polypeptide as described herein as a vaccine for the treatment or prevention of necrotic enteritis in poultry or for the treatment or prevention of *Clostridium perfringens* infection in poultry.

A further aspect of the present invention provides an antibody which binds selectively to an immunogenic polypeptide as described herein. In at least one embodiment, the antibody is a poultry antibody. In at least one embodiment, the antibody can be a polyclonal antibody, a monoclonal antibody, a chimeric antibody, a single chain antibody or an antibody fragment that retains the property of selective binding to an immunogenic polypeptide as described herein. The term "antibody fragment" as used herein is intended to include but not be limited to Fab, Fab', F(ab')$_2$, scFv, dsFv, ds-scFv, dimers, minibodies, diabodies, and multimers thereof and bispecific antibody fragments. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

Methods of preparing and characterizing such antibodies and fragments thereof are well known in the art and can be readily carried out by the skilled person without undue effort. For example, polyclonal antisera or monoclonal antibodies can be made using standard methods. A mammal, (e.g., a mouse, hamster, or rabbit), bird (e.g. poultry) or other animal can be immunized with an immunogenic form of the present immunogenic polypeptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogenic agent as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Hybridoma cells can be screened immunochemically for production of antibodies specifically reactive with an immunogenic polypeptide as described herein and the monoclonal antibodies can be isolated. Therefore, the disclosure also contemplates hybridoma cells secreting monoclonal antibodies with specificity for an immunogenic polypeptide as described herein.

Specific antibodies, or antibody fragments reactive against an immunogenic polypeptide as described herein may also be generated by screening expression libraries encoding immunoglobulin genes, or portions thereof, expressed in bacteria with peptides produced from nucleic acid molecules as described herein. For example, complete Fab fragments, VH regions and FV regions can be expressed in bacteria using phage expression libraries.

In another aspect, the present invention provides a method of detecting infection of poultry by a strain of *Clostridium perfringens* associated with necrotic enteritis, wherein the method includes obtaining a biological sample from the poultry and detecting in the biological sample the presence of an antibody which binds selectively to an immunogenic polypeptide as described herein. In at least one embodiment, the biological sample is a blood sample. In at least one embodiment, the sample is a fecal sample. In at least one embodiment, the detection includes measurement of the amount or concentration of antibody present in the biological sample, using methods well known by those skilled in the art.

Yet another aspect of the present invention provides a method of detecting an immunogenic polypeptide as described herein comprising exposing the immunogenic polypeptide to an antibody which binds selectively to the immunogenic polypeptide and detecting binding of the immunogenic polypeptide to the antibody. In at least one embodiment, the immunogenic polypeptide can be an isolated *Clostridium perfringens* pilus polypeptide as described herein. In at least one embodiment, the immunogenic polypeptide can be an assembled pilus attached to the surface of a *Clostridium perfringens* bacterial cell. Such embodiments of the method can be useful for identifying and detecting strains of *Clostridium perfringens* which are capable of producing necrotic enteritis in poultry.

As used herein, the terms "about" or "approximately" as applied to a numerical value or range of values are intended to mean that the recited values can vary within an acceptable degree of error for the quantity measured given the nature or precision of the measurements, such that the variation is considered in the art as equivalent to the recited values and provides the same function or result. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "substantially" refers to the complete or nearly complete extent or degree of an action, characteristic, property, state, structure, item, or result. For example, two substances which have "substantially" the same properties would have completely identical properties or would have properties which are so nearly completely the same that the differences are not measurable or significant. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

EXAMPLES

Other features of the present invention will become apparent from the following non-limiting examples which illustrate, by way of example, the principles of the invention.

Example 1: Production of Purified Recombinant Pilus-Associated Polypeptides from *Clostridium perfringens*

Coding regions for the three pilus subunits (cnaA, fimA and fimB) were codon-optimized and truncated to exclude the predicted N-terminal signal peptides and C-terminal cell wall sorting signal LPXTG (SEQ ID NO: 16) transmembrane domains. The C-terminal domain is a hydrophobic region predicted to be removed during pilus assembly. The truncated codon-optimized coding regions were synthesized (Integrated DNA Technologies, Coralville, USA), cloned into the pET28a expression vector (MilliporeSigma, Etobicoke, Ontario, Canada) by In-Fusion™ cloning according to the manufacturer's instructions (Takara Bio USA, Mountain View, Calif., USA), sequence-verified, and then transformed into *E. coli* BL21 cells. Transformed colonies were grown at 37° C. for 18 h with shaking in 1 L LB broth supplemented with 50 μg/ml kanamycin and 1 mM IPTG. The culture was pelleted and resuspended in 20 ml of binding buffer (20 mM $NaPO_4$, 0.5M NaCl, 30 mM imidazole) and lysed by sonication for 10 min on ice (10 s pulses, 20 s pauses). The cell lysate was purified under native conditions on a HisTrap™ FF Crude column (GE Healthcare, Montreal, Canada) using a gradient of 50 to 500 mM imidazole on an ÄKTA™ prime plus system. One ml fractions were collected, and fractions exhibiting a 280 nm peak were pooled and concentrated with Pierce™ Protein Concentrators (9K molecular weight cut-off) (Fisher Scientific, Unionville, Ontario, Canada) and desalted using Zeba™ Spin 7K molecular weight cut-off desalting columns (Fisher Scientific). Quantitation of the purified proteins was performed using the BCA (bicinchoninic acid) Protein Assay kit (Fisher) according to the manufacturer's instructions. Polypeptides were visualized by SDS-PAGE and COOMASSIE staining.

The truncated sequences resulted in high levels of expression of histidine (His)-tagged polypeptides, as evidenced by the SDS-PAGE gels shown in FIGS. 2A (CnaA), 2B (FimA), 2C (FimB) and 2D (pooled fractions of CnaA, FimA and FimB, following concentration and desalting). These increased levels of expression may be due to increased solubility of the resulting polypeptides.

Table 1 shows the sequences of the full-length, codon-optimized and truncated gene sequences, along with the sequences of the full-length subunit polypeptides and the expressed truncated and His-tagged subunit polypeptides.

TABLE 1

Sequences of pilus subunit genes and polypeptides

| Sequence | cnaA | fimA | fimB |
|---|---|---|---|
| Full length | ATGAAAATAAATAAAAAAATTTTTAGCATGCTAT | ATGATAAACAAGAAAAAA | ATGGAAACAAAG |
| gene | TTATGGTTATTGTACTTTTTACATGCATATCATC | TTAAGTGCATTATTATTA | AAAATAAGAAAC |
| | AAATTTTTCTGTTTCTGCTTCTTCTATTCAAAGA | AGTGGAGCAATGTTTATG | AAAATCCTTATG |
| | GGAAGAGATATCAGTAATGAGGTAGTTACAAGCC | AGTATGAATACAAATGTA | GCTATCGTAGCA |
| | TAGTGGCTACTCCAAATAGTATAAATGATGGTGG | TTCGCATCAAATTTACCT | TTGAGCTTTATA |
| | AAACGTTCAGGTTCGTTTGGAATTTAAAGAAAAT | TCTGGAGGGGTAGAAGGT | TTGCTTCCAAAC |
| | CATCAAAGATATATACAAAGTGGAGATACTATAA | ACAGAACAGAATCCTGCA | ACTAGAGTATAT |
| | CTGTCAAATGGACAAATTCAGGGGAAGTATTTTT | AAAGCAACAATTACAAAG | GCTACTGAAAAT |
| | TGAAGGATATGAAAAAACAATTCCACTTTATATA | AATTTTGAATTTCCAGAA | ACAGCAAATATT |
| | AAAGACCAAAATGTTGGTCAAGGAGTAATAGAGA | GGTATTAATACACCTAGT | CCTTTGATAGTT |
| | AAACAGGTGCAACACTTACATTTAATGATAAAAT | GCAACATTCAAGTTTACA | AGACAGGAATTT |
| | AGATAAATTAGATGATGTTGGTGGATGGGCAACA | GCAGAAAAAATAACTAAT | AATGTATATACG |
| | TTTACTTTGCAAGGAAGAAACATTACCTCAGGTA | GATGCGCCAGATGCAACA | AAAGATTCAAAA |
| | ATCATGAACACACAGGAATAGCATATATTATATC | ATTGGAGATATTAATTAT | GCAATAGACATG |
| | TGGTTCAAAGCGGGCAGATGTAAATATAACCAAA | ACACAAGGGGATAATGGA | ATTGGAAAATAC |
| | CCAGAATCAGGTACAACTAGTGTATTCTATTATA | ACTTTATCAAATGGAAAA | GAGCTAAAGGCA |
| | AAACAGGTAGTATGTATACCAATGATACAAATCA | TATAGTGTAAAGAAAACA | ATAAGTGAAAAT |
| | TGTCAATTGGTGGTTACTGGTGAATCCAAGCAAG | ACTGAAATTACTTTTGGA | GCCCCTATGCCA |
| | GTATATTCTGAAAAAAACGTTTATATTCAAGATG | AATTTCCCACATGCAGGA | GAAGAAAGTAAA |
| | AAATCCAAGGCGGACAAACATTAGAACCTGATTC | GAATATGATTATAATGTA | AATGGAAGTTTT |
| | TTTTGAAATAGTAGTAACTTGGTATGATGGTTAT | AAAGAAACGAATGAGGGA | ATCTTTAATATA |
| | GTAGAAAAGTTTAAAGGAAAAGAAGCGATAAGGG | GTAGGTGGTATTACATAT | GATGGAAATGAT |
| | AATTCCATAATAAATATCCAAATTCAAATATATC | GATACAAAAGAATACAAA | AAGCAGTTTACT |
| | GGTATCAGAAAATAAAATAACAGTAAACATTTCA | GTTCATGTGTATGTTGCA | ATTCCATTAGCT |
| | CAAGAGGATTCCACACAAAAGTTTATTAATATTT | AATAGTAACGCTATGGAT | TATACACATGGT |
| | TTTATAAAACTAAGATTACAAATCCGAAACAAAA | GGAAAAACTTATGTAAAA | GGTGTGTATATC |
| | AGAATTCGTTAATAATACAAAAGCATGGTTTAAA | GCCATTACATCAGAAAAT | TATCAAATTCAA |
| | GAGTATAATAAGCCAGCTGTAAATGGAGAATCCT | GGAGGTGAAAAAGCTCCA | CAGATAACGCAA |
| | TTAACCATAGCGTACAAAATATTAATGCAGATGC | ATTGAGTTTGTTAATACA | TCTAAAGATAAT |
| | TGGAGTTAATGGAACTGTAAAAGGCGAATTAAAA | TATAAAAAGGACACTTCT | TACATATATGAT |
| | ATCATAAAAACATTAAAAGATAAAAGTATTCCAA | TTACTTATAGAAAAGAAT | AAAAATAGCTAT |
| | TTAAAGATGTTCAGTTTAAGATGAGAAGAGTTGA | GTAATAGGAGATTTAGCT | AAGATAACTGTA |
| | TAATACAGTTATCAAAGATGGTAAAAAAGAATTA | GACTTAACAAAACAGTTT | TATGTAAAAAAT |
| | TTACTAACAACTGATGATAAAGGTATTGCAAATG | GAGTTTCAGATTAATTTA | GCAGAAAATAAT |
| | TAAAAGGTCTTCCTGTAGGAAAATATGAAGTAAA | AAAAAATCAGCAACATCT | CATTTAATACCA |

TABLE 1-continued Sequences of pilus subunit genes and polypeptides

| Sequence | cnaA | fimA | fimB |
|---|---|---|---|
| | AGAGATTTCAGCTCCAGAATGGATTGCTTTTAAT<br>CCTCTTATTGCACCAAAATTGGAATTCACAATAT<br>CAGATCAGGACACAGAAGGCAAATTGTGGGCTGT<br>TGAAAATGAATTAAAGACAATTTCAATTCCGGTT<br>GAAAAGGTCTGGGTAGGACAAACTAGTGAACGAG<br>CAGAAATCAAGCTTTTTGCAGATGGTATTGAAGT<br>AGACAAAGTGATTTTAAATGCAGATAACAATTGG<br>AAACACACATTTGAAAATAAACCTGAATATAATT<br>CAGAAACAAAACAGAAAATCAATTATTCTGTGTC<br>AGAGACAACTATTTCTGGATATGAAAGCAATATC<br>ACAGGCGATGCTAAGAATGGTTTTATTGTAACCA<br>ATACAGAACTTCCTGATTTGACTATTGGTAAAGA<br>AGTTATAGGAGAATTGGGTGACAAGACGAAGGTA<br>TTTAACTTTGAGCTTACATTAAAGCAAGCAGATG<br>GAAAGCCTATCAATGGTAAATTTAATTACATTGG<br>TAGTGTAGATGACAGGTACAAAAAAGAAAGCATA<br>AAGCCTTCTGATGGTGAGATTACTTTTATAGAAG<br>GAAAAGCAACTATAACTTTATCACATGGACAAGA<br>GATTACAATCAAGGATTTACCATATGGGGTTACA<br>TATAAAGTTATGGAAAAAGAAGCTAATGAAAATG<br>GCTATTTAACTACCTATAATGGAAATAACGAAGT<br>CACAACAGGTGAATTGAAACAGGATACAAAAGTA<br>CAGGTAGTTAACAACAAAGAGTTTGTTCCAACAA<br>CTGGTATATCAACCACAACAGAGCAAGGTACAAT<br>GGTTGGAATGGTGATTTTTTCTATAGGAATACTT<br>ATGGTCATGATTGTAGTTCTTTTACAATTGAATA<br>AGGACTGAAAAGATGA (SEQ ID NO: 1) | GACATAACAAAATTCGAA<br>GGAAATATTATTAGAAAA<br>GTAACATATACAGCTGAA<br>AATACAGAAACTTTTAAA<br>TTAGCAAATGGAGATAAA<br>CTTAAGTTTGAAAGTATT<br>CCAGCAGGAACAAAATAT<br>GAAGTAAAAGAGATAGGT<br>GCTAGTGATGGATATACA<br>CCTTCTATAACAGTAATT<br>GAAAATGGAAATGAGACT<br>TCTAATAATCGTACGGTA<br>GCTGAAAAAGATGGTATA<br>TCATCAAGTCAAATTCT<br>AATGATAACTTAATTGGT<br>GAAGGTGAAAACAAAGTA<br>ACATTTACAAACACATAT<br>AATGACAAACCTATCACA<br>GGTATTGTTATGAATAAT<br>ATTCCATTTATTCTAATG<br>ATTAGTTTTGCTGTCCTT<br>GGATTTGGTGCTTTAGCT<br>ATTATAAAAGACGTAAA<br>ACTATAAGATAAA<br>(SEQ ID NO: 2) | CAAATTATTGTG<br>AAAAATGAAAAT<br>AATGAAAAATGT<br>GAAGAAATATGT<br>ATTTATAACATT<br>TACAAACAAAAA<br>AATAAAATTAAT<br>GAGATTTCTAAA<br>ACACCATATAAG<br>CCAAATGGAATA<br>AATGTTCCTAAA<br>ACAGGCGATACC<br>ACAAACATTGGA<br>TTTTATATTGTA<br>ATACTTATAATT<br>TCACTTGGATTA<br>CTTGTGGTATTG<br>AAATGAAAGAA<br>TATAAAAGAGA<br>AAAAAGAATAA<br>(SEQ ID NO: 3) |
| Codon optimized gene | ATGAAGATCAACAAGAAGATCTTCAGCATGTTAT<br>TTATGGTCATTGTGCTGTTCACCTGTATCAGCTC<br>TAACTTCAGTGTGAGCGCGTCAAGCATCCAGCGC<br>GGCCGGGACATCAGCAACGAGGTGGTGACATCGC<br>TCGTAGCTACCCCGAATAGCATCAACGATGGTGG<br>TAACGTCCAAGTGCGTCTGGAATTTAAAGAGAAT<br>CACCAGCGGAACATTCAGTCCGGCGACACGATTA<br>CGGTCAAATGGACTAACTCAGGTGAGGTCTTTTT<br>TGAAGGCTACGAAAAACCATCCCGCTGTATATC<br>AAGGATCAGAACGTTGGCCGGCGGTTATTGAAA<br>AAACCGGTGCAACATTAACATTAACGATAAGAT<br>CGACAAATTAGATGATGTCGGCGGCTGGGCCACA<br>TTCACGCTCCAGGGTCGCAATATTACTTCAGGAA<br>ATCATGAGCATACTGGTATTGCTACATTATCTC<br>GGGTAGCAAACGTGCGGACGTTAACATCACAAAA<br>CCTGAATCCGGAACAACGTCTGTGTTTTACTACA<br>AGACGGGTTCGATGTACACCAATGACACAAATCA<br>TGTGAATTGGTGGCTGCTGGTTAACCCGAGCAAA<br>GTATACTCTGAGAAAAATGTCTATATTCAGGATG<br>AAATTCAAGGCGGTCAGACCCTGGAGCCGGACAG<br>TTTTTGAAATCGTCGTTACATGGTACGATGGTTAT<br>GTGGAAAAATTTAAAGGTAAAGAAGCGATCCGGG<br>AGTTCCACAATAAATATCCGAATAGTAATATCTC<br>GGTCAGTGAAAATAAAATCACGGTAAATATTTCG<br>CAAGAAGATTCCACCCAAAAATTCATTAACATCT<br>TTTACAAGACTAAAATCACCAACCCGAAGCAGAA<br>AGAATTTGTAAACAACACCAAAGCCTGGTTCAAA<br>GAGTACAATAAGCCGGCGGTTAACGGTGAAAGTT<br>TTAATCACAGTGTGCAGAATATCAACGCAGATGC<br>CGGGGTAAATGGTACTGTTAAAGGTGAATTGAAA<br>ATTATCAAAACCCTGAAAGATAAAAGTATTCCGA<br>TCAAGGATGTGCAGTTTAAGATGCGCCGCGTGGA<br>TAATACCGTTATTAAAGACGGCAAGAAAGAGCTG<br>CTGTTGACCACAGATGATAAAGGGATTGCAAACG<br>TGAAAGGTCTGCCAGTCGGGAAATACGAAGTCAA<br>AGAAATCAGTGCGCCTGAGTGGATCGCCTTCAAT<br>GCACTGATTGCGCCCAAACTTGAATTTACGATCA<br>GCGATCAAGACACAGAGGGGAAATTATGGGCAGT<br>GGAAACGAACTCAAAACCATCTCGATTCCGGTC<br>GAAAAAGTCTGGGTAGGTCAGACGAGTGAACGGG<br>CGGAGATCAAACTGTTTGCGGATGGAATTGAAGT<br>TGATAAGGTGATCCTGAACGCGGATAATAATTGG<br>AAGCACACCTTTGAGAATAAACCGAATATAACT<br>GCGAGACTAAACAAAAATCAACTATAGTGTGAG<br>CGAAACTACCATCAGTGGCTATGAATCAAATATT<br>ACTGGCGATGCGAAAACGGATTTATTGTCACCA<br>ACACAGAACTGCCTGATTTGACGATCGGGAAAGA<br>GGTAATCGGCGAACTCGGCGATAAAACCAAGGTA | ATGATTAATAAAAAGAAA<br>CTGTCGGCGCTGCTCTTA<br>AGCGGGGCCATGTTTATG<br>AGCATGAACACGAATGTG<br>TTCGCGTCTAACCTCCCA<br>TCGGGTGGTGTGGAGGGC<br>AACACCGCTAAT<br>ATCCCGTTAATT<br>GTACGCCAAGAA<br>TTTAATGTTTAC<br>ACTAAAGATTCT<br>AAAGCCATTGAC<br>ATGATCGGAAAA<br>TATGAATTAAAA<br>GCCATTTCTGAG<br>AACGCTCCCATG<br>CCGGAGGAATCA<br>AAAAATGGTAGC<br>TTTATTTTTAAC<br>ATCGACGGTAAT<br>GATAAACAGTTT<br>ACTATTCCGCTG<br>GCGTACACTCAC<br>GGTGGCGTCTAC<br>ATCTATCAAATC<br>CAGCAAATTACC<br>CAGAGCAAGGAT<br>AACTACATCTAC<br>GATAAAACAGC<br>TATAAAATCACG<br>GTATATGTCAAG<br>AACGCAGAAAAC<br>AATCATCTGATC<br>CCGCAGATTATT<br>GTAAAAAATGAG<br>AACAATGAAAAA<br>TGTGAAGAAATC<br>TGCTTCTACAAT<br>ATCTACAAACAG<br>AAAAACAAGATC<br>AATGAGATCTCT<br>AAAACCCCCTAT<br>AAGCCGAATGGT<br>ATTAATGTCCCG<br>AAAACGGGTGAT<br>ACCACGAACATC<br>GGATTCTACATT<br>GTGATCTTGATT<br>ATTTCCCTGGGC | |

TABLE 1-continued

Sequences of pilus subunit genes and polypeptides

| Sequence | cnaA | fimA | fimB |
|---|---|---|---|
| | TTCAACTTTGAACTGACACTTAAGCAGGCTGACG<br>GAAAAGCCCATTAACGGGAAATTTAACTATATTGG<br>TTCGGTGGATGATCGTTATAAGAAGGAATCGATT<br>AAGCCTAGCGATGGGGAAATTACGTTCATCGAGG<br>GAAAAGCAACGATTACCCTCTCCCACGGACAAGA<br>GATCACCATTAAGGACCTTCCGTATGGTGTGACC<br>TATAAAGTCATGGAAAAGAAGCCAACGAGAATG<br>GATATTTAACCACTTACAACGGAAATAACGAAGT<br>GACCACCGGGGAGTTGAAACAGGATACGAAAGTA<br>CAAGTGGTTAATAATAAAGAATTCGTCCCGACAA<br>CCGGGATCAGCACCACCACCGAACAGGGAACCAT<br>GGTCGGGATGGTGATCTTTAGCATCGGTATTCTC<br>ATGGTAATGATTGTCGTTCTGCTGCAGCTGAATA<br>AAGGACTGAAACGC (SEQ ID NO: 4) | GCCGAAAAAGATGGAATC<br>TCTAGCAAAAGCAACTCG<br>AACGACAATTTAATCGGC<br>GAAGGCGAAAATAAAGTG<br>ACCTTTACCAATACGTAC<br>AACGATAAACCAATCACG<br>GGAATCGTAATGAATAAT<br>ATTCCGTTCATTCTTATG<br>ATTAGCTTTGCCGTTCTT<br>GGCTTCGGTGCATTAGCG<br>ATCATTAAACGCCGCAAA<br>ACCATCCGCCCCATCGAT<br>ACGCGT<br>(SEQ ID NO: 5) | CTGCTGGTGGTC<br>TTGAAGTGGAAA<br>GAATATAAAAAA<br>CGTAAGAAGGAA<br>(SEQ ID NO: 6) |
| Truncated gene | TCAAGCATCCAGCGCGGCCGGGACATCAGCAACG<br>AGGTGGTGACATCGCTCGTAGCTACCCCGAATAG<br>CATCAACGATGGTGGTAACGTCCAAGTGCGTCTG<br>GAATTTAAAGAGAATCACCAGCGGAACATTCAGT<br>CCGGCGACACGATTACGGTCAAATGGACTAACTC<br>AGGTGAGGTCTTTTTTGAAGGCTACGAAAAAACC<br>ATCCCGCTGTATATCAAGGATCAGAACGTTGGCC<br>AGGCGGTTATTGAAAAAACCGGTGCAACATTAAC<br>ATTCAACGATAAGATCGACAAATTAGATGATGTC<br>GGCGGCTGGGCCACATTCACGCTCCAGGGTCGCA<br>ATATTACTTCAGGAAATCATGAGCATACTGGTAT<br>TGCGTACATTATCTCGGGTAGCAAACGTGCGGAC<br>GTTAACATCACAAAACCTGAATCGGAACAACGT<br>CTGTGTTTTACTACAAGACGGGTTCGATGTACAC<br>CAATGACACAAATCATGTGAATTGGTGGCTGCTG<br>GTTAACCCGAGCAAAGTATACTCTGAGAAAAATG<br>TCTATATTCAGGATGAAATTCAAGGCGGTCAGAC<br>CCTGGAGCCGGACAGTTTTGAAATCGTCGTTACA<br>TGGTACGATGGTTATGTGAAAAAATTTAAAGGTA<br>AGAAGCGATCCGGGAGTTCCACAATAAATATCC<br>GAATAGTAATATCTCGGTCAGTGAAAATAAAATC<br>ACGGTAAATATTTCGCAAGAAGATTCCACCCAAA<br>AATTCATTAACATCTTTTACAAGACTAAAATCAC<br>CAACCCGAAGCAGAAAGAATTTGTAAACAACACC<br>AAAGCCTGGTTCAAAGAGTACAATAAGCCGGCGG<br>TTAACGGTGAAAGTTTTAATCACAGTGTGCAGAA<br>TATCAACGCAGATGCCGGGGTAAATGTACTGTT<br>AAAGGTGAATTGAAATTATCAAAACCCTGAAAG<br>ATAAAAGTATTCCGATCAAGGATGTGCAGTTTAA<br>GATGCGCCGCGTGGATAATACCGTTATTAAAGAC<br>GGCAAGAAAGAGCTGCTGTTGACCACAGATGATA<br>AAGGGATTGCAAACGTGAAAGGTCTGCCAGTCGG<br>GAAATACGAAGTCAAAGAAATCAGTGCGCCTGAG<br>TGGATCGCCTTCAATCCACTGATTGCGCCCAAAC<br>TTGAATTTACGATCAGCGATCAAGCACACAGAGGG<br>GAAATTATGGGCAGTGGAAAACGAACTCAAAACC<br>ATCTCGATTCCGGTCGAAAAAGTCTGGGTAGGTC<br>AGACGAGTGAACGGGCGGAGATCAAACTGTTTGC<br>GGATGGAATTGAAGTTGATAAGGTGATCCTGAAC<br>GCGGATAATAATTGGAAGCACACCTTTGAGAATA<br>AACCCGAATATAACTCCGAGACTAAACAAAAAAT<br>CAACTATAGTGTGAGCGAAACTACCATCAGTGGC<br>TATGAATCAAATATTACTGGCGATGCGAAAAACG<br>GATTTATTGTCACCAACACAGAACTGCCTGATTT<br>GACGATCGGGAAAGAGGTAATCGGCGAACTCGGC<br>GATAAAACCAAGGTATTCAACTTTGAACTGCAC<br>TTAAGCAGGCTGACGGAAAGCCCATTAACGGGAA<br>ATTTAACTATATTGGTTCGGTGGATGATCGTTAT<br>AAGAAGGAATCGATTAAGCCTAGCGATGGGGAAA<br>TTACGTTCATCGAGGGAAAAGCAACGATTACCCT<br>CTCCCACGGACAAGAGATCACCATTAAGGACCTT<br>CCGTATGGTGTGACCTATAAAGTCATGGAAAAAG<br>AAGCCAACGAGAATGGATATTTAACCACTTACAA<br>CGGAAATAACGAAGTCACCACCGGGGAGTTGAAA<br>CAGGATACGAAAGTACAAGTGGTTAATAATAAAG<br>AATTCGTCCCGACAACC (SEQ ID NO: 7) | TCTAACCTCCCATCGGGT<br>GGTGTGGAGGTGCACCGAA<br>CAAAACCCAGCGAAAGCG<br>ACAATCACGAAAAACTTC<br>GAGTTTCCGGAAGGTATT<br>AATACACCCAGCGCGACA<br>TTCAAATTTACCGCCGAA<br>ATTGACATGATC<br>GGAAAATATGAA<br>TTAAAAGCCATT<br>TCTGAAGAACGCT<br>CCCATGCCGGAG<br>GAATCAAAAAAT<br>GGTAGCTTTATT<br>TTTAACATCGAC<br>GGTAATGATAAA<br>CAGTTTACTATT<br>CCGCTGGCGTAC<br>ACTCACGGTGGC<br>GTCTACATCTAT<br>CAAATCCAGCAA<br>ATTCCCAGAGC<br>AAGGATAACTAC<br>ATCTACGATAAA<br>AACAGCTATAAA<br>ATCACGGTATAT<br>GTCAAGAACGCA<br>GAAAACAATCAT<br>CTGATCCCGCAG<br>ATTATTGTAAAA<br>AATGAGAACAAT<br>GAAAAATGTGAA<br>GAAATCTGCTTC<br>TACAATATCTAC<br>AAACAGAAAAAC<br>AAGATCAATGAG<br>ATCTCTAAAACC<br>CCCTATAAGCCG<br>AATGGTATTAAT<br>GTCCCGAAAACG<br>(SEQ ID NO: 9) | |
| | | GGCAACGAAACCTCAAAT<br>AACCGCACTGTAGCCGAA<br>AAAGATGGAATCTCTAGC<br>AAAAGCAACTCGAACGAC<br>AATTTAATCGGCGAAGGC<br>GAAAATAAAGTGACCTTT<br>ACCAATACGTACAACGAT<br>AAACCAATCACG<br>(SEQ ID NO: 8) | |
| Full-length polypeptide | MKINKKIFSMLFMVIVLFTCISSNFSVSASSIQR<br>GRDISNEVVTSLVATPNSINDGGNVQVRLEFKEN<br>HQRNIQSGDTITVKWTNSGEVFFEGYEKTIPLYI<br>KDQNVGQAVIEKTGATLTFNDKIDKLDDVGGWAT | MINKKKLSALLLSGAMFM<br>SMNTNVFASNLPSGGVEG<br>TEQNPAKATITKNFEFPE<br>GINTPSATFKFTAEKITN | METKKIRNKILM<br>AIVALSFILLPN<br>TRVYATENTANI<br>PLIVRQEFNVYT |

TABLE 1-continued

Sequences of pilus subunit genes and polypeptides

| Sequence | cnaA | fimA | fimB |
|---|---|---|---|
| | FTLQGRNITSGNHEHTGIAYIISGSKRADVNITK PESGTTSVFYYKTGSMYTNDTNHVNWWLLVNPSK VYSEKNVYIQDEIQGGQTLEPDSFEIVVTWYDGY VEKFKGKEAIREFHNKYPNSNISVSENKITVNIS QEDSTQKFINIFYKTKITNPKQKEFVNNTKAWFK EYNKPAVNGESFNHSVQNINADAGVNGTVKGELK IIKTLKDKSIPIKDVQFKMRRVDNTVIKDGKKEL LLTTDDKGIANVKGLPVGKYEVKEISAPEWIAFN PLIAPKLEFTISDQDTEGKLWAVENELKTISIPV EKVWVGOTSERAEIKLFADGIEVDKVILNADNNW KHTFENKPEYNSETKQKINYSVSETTISGYESNI TGDAKNGFIVTNTELPDLTIGKEVIGELGDKTKV FNFELTLKQADGKPINGKFNYIGSVDDRYKKESI KPSDGEITFIEGKATITLSHGQEITIKDLPYGVT YKVMEKEANENGYLTTYNGNNEVTTGELKQDTKV QVVNNKEFVPTTGISTTTEQGTMVGMVIFSIGIL MVMIVVLLQLNKGLKR (SEQ ID NO: 10) | DAPDATIGDINYTQGDNG TLSNGKYSVKKTTEITFG NFPHAGEYDYNVKETNEG VGGITYDTKEYKVHVYVA NSNAMDGKTYVKAITSEN GGEKAPIEFVNTYKKDTS LLIEKNVIGDLADLTKQF EFQINLKKSATSDITKFE GNIIRKDGKIEPVTYTAE NTETFKLANGDKLKFESI PAGTKYEVKEIGASDGYT PSITVIENGNETSNNRTV AEKDGISSKSNSNDNLIG EGENKVTFTNTYNDKPIT GIVMNNIPFILMISFAVL GFGALAIIKRRKTIR (SEQ ID NO: 11) | KDSKAIDMIGKY ELKAISENAPMP EESKNGSFIFNI DGNDKQFTIPLA YTHGGVYIYQIQ QITQSKDNYIYD KNSYKITVYVKN AENNHLIPQIIV KNENNEKCEEIC FYNIYKQKNKIN EISKTPYKPNGI NVPKTGDTTNIG FYIVILIISLGL LVVLKWKEYKKR KKE (SEQ ID NO: 12) |
| Expressed truncated polypeptide | MGSSHHHHHHSSGLVPRGSHMASMTGGQQMGRGS EFSSIQRGRDISNEVVTSLVATPNSINDGGNVQV RLEFKENHQRNIQSGDTITVKWTNSGEVFFEGYE KTIPLYIKDQNVGQAVIEKTGATLTFNDKIDKLD DVGGWATFTLQGRNITSGNHEHTGIAYIISGSKR ADVNITKPESGTTSVFYYKTGSMYTNDTNHVNWW LLVNPSKVYSEKNVYIQDEIQGGQTLEPDSFEIV VTWYDGYVEKFKGKEAIREFHNKYPNSNISVSEN KITVNISQEDSTQKFINIFYKTKITNPKQKEFVN NTKAWFKEYHKPAVNGESFNHSVQNINADAGVNG TVKGELKIIKTLKDKSIPIKDVQFKMRRVDNTVI KDGKKELLLTTDDKGIANVKGLPVGKYEVKEISA PEWIAFNPLIAPKLEFTISDQDTEGKLWAVENEL KTISIPVEKVWVGQTSERAEIKLFADGIEVDKVI LNADNNWKHTFENKPEYNSETKQKINYSVSETTI SGYESNITGDAKNGFIVTNTELPDLTIGKEVIGE LGDKTKVFNFELTLKQADGKPINGKFNYIGSVDD RYKKESIKPSDGEITFIEGKATITLSHGQEITIK DLPYGVTYKVMEKEANENGYLTTYNGNNEVTTGE LKQDTKVQVVNNKEFVPTTVDKLAAALEHHHHHH (SEQ ID NO: 13) | MGSSHHHHHHSSGLVPRG SHMASMTGGQQMGRGSEF SNLPSGGVEGTEQNPAKA TITKNFEFPEGINTPSAT FKFTAEKITNDAPDATIG DINYTQGDNGTLSNGKYS VKKTTEITFGNFPHAGEY DYNVKETNEGVGGITYDT KEYKVHVYVANSNAMDGK TYVKAITSENGGEKAPIE FVNTYKKDTSLLIEKNVI GDLADLTKQFEFQINLKK SATSDITKFEGNIIRKDG KIEPVTYTAENTETFKLA NGDKLKFESIPAGTKYEV KEIGASDGYTPSITVIEN GNETSNNRTVAEKDGISS KSNSNDNLIGEGENKVTF TNTYNDKPITVDKLAAAL EHHHHHH (SEQ ID NO: 14) | MGSSHHHHHHSS GLVPRGSHMASM TGGQQMGRGSEF TENTANIPLIVR QEFNVYTKDSKA IDMIGKYELKAI SENAPMPEESKN GSFIFNIDGNDK QFTIPLAYTHGG VYIYQIQQITQS KDNYIYDKNSYK ITVYVKNAENNH LIPQIIVKNENN EKCEEICFYNIY KQKNKINEISKT PYKPNGINVPKT VDKLAAALEHHH HHH (SEQ ID NO: 15) |

Example 2: Preparation of *Clostridium perfringens* Strain CP1 Pilus Subunit Null-Mutants The three pilus subunit genes (cnaA, fimA and fimB) were each insertionally inactivated in the virulent *Clostridium perfringens* strain CP1 by ClosTron mutagenesis (Heap, J. T., et al, *Methods Mol. Biol.* (2010), 646: 165-182), essentially as described previously (Yu, Q., Lepp, D., Mehdizadeh Gohari, I., Wu, T., Zhou, H., Yin, X., Yu, H., Prescott, J. F., Nie, S. P., Xie, M. Y., Gong, J., 2017. The Agr-like quorum sensing system is required for necrotic enteritis pathogenesis in poultry caused by *Clostridium perfringens*. *Infection and Immunity* 85(6): e00975-16), to generate CP1 null-mutants for each of the pilus subunit genes (CP1ΔcnaA, CP1ΔfimA, and CP1ΔfimB). Briefly, ClosTron intron-targeting regions were designed to insert at the following gene positions using the Perutka algorithm implemented at www.clostron.com: base-pair (bp) 183 of the cnaA sense strand, bp 231 of the fimA sense strand, and bp 273 of the fimB sense strand. The intron-targeting regions were synthesized and cloned into ClosTron plasmid pMTL007C-E2 by DNA 2.0 (Menlo Park, Calif., USA). The resultant plasmids were separately electroporated into CP1 as described previously with minor modifications (Jirásková A, Vítek L, Fevery J, Ruml T, Branny P. 2005. Rapid protocol for electroporation of *Clostridium perfringens*. J Microbiol Methods 62:125-127). Briefly, after growth at 37° C. anaerobically overnight in 5 ml TGY broth (3% tryptone, 2% glucose, 1% yeast extract), CP1 was subcultured into 50 ml TGY and grown to exponential phase (optical density at 600 nm [OD 600], 0.8). The cells were harvested by centrifugation at 6,000 g for 10 min at 20° C. and washed once in 10 ml sucrose electroporation buffer (SEB) (272 mM sucrose, 1 mM MgCl$_2$, 5 mM Na$_2$HPO$_4$, pH 7.4) and then resuspended in 5 ml SEB. Aliquots (0.2 ml) were mixed with 2 μg concentrated plasmid DNA in prechilled cuvettes (0.2-cm gap), and plasmid DNA was introduced into the cells by electroporation (1,000 V, 25 F) using a Bio-Rad GenePulser Xcell apparatus (Bio-Rad, Hercules, Calif., USA). Immediately after transformation, the mixture was transferred into 1 ml of TGY broth and incubated anaerobically at 37° C. for 3 h, followed by plating onto TGY agar containing 15 μg/ml thiamphenicol anaerobically at 37° C. overnight for selecting transformants. The resulting colonies were subcultured onto TGY agar containing 10 μg/ml erythromycin for selecting integrants and then passaged for 10 consecutive days to cure the shuttle vector. Those clones resistant to erythromycin but sensitive to thiamphenicol were chosen for further analysis.

Example 3: Animal Trials

Two vaccination trials were carried out to assess the ability of the three purified His-tagged recombinant pilus subunits to protect against necrotic enteritis (NE) in a chicken challenge model. Commercial day-old male White Plymouth Rock broiler chickens were randomly divided into experimental groups (n=15-17) and housed in separate rooms within an isolation unit. A summary of the trial designs is shown in Table 2. In addition, the CP1ΔfimA, and CP1ΔfimB mutants were assessed for virulence in the same model.

TABLE 2

Summary of vaccination trial designs

| Trial | Antigens tested | Vaccination days | Injection site | Serum collection days | CP1 challenge days | Day of euthanasia |
|---|---|---|---|---|---|---|
| 1 | CnaA, FimA | 8, 20 | i.m. | 8, 20, 31 | 28, 29 | 31 |
| 2 | CnaA, FimB, CnaA + FimA + FimB | 7, 14, 19 | s.c. | 7, 19, 29 | 26, 27 | 29 |

Trial 1:

The first trial included three groups of 18 birds vaccinated with either adjuvant-only control, CnaA or FimA. Each bird was injected intramuscularly (i.m.) in the pectoral muscle with 200 μl phosphate-buffered saline (PBS) containing Quil-A™ adjuvant (50 μg) and recombinant pilus polypeptide (50 μg) at days 8 and 20, and birds were euthanized on day 31.

Serum was collected from five birds from each group at days 8 (prior to immunization), and at days 20 and 31 (after immunization). Serum IgY titres against CnaA and FimA were determined by ELISA (enzyme-linked immunosorbent assay). *C. perfringens* recombinant pilus polypeptides were diluted to 10 μg/ml in 50 mM carbonate/bicarbonate coating buffer at pH 9.6, and 100 μl was added to each well of a 96-well MaxiSorp™ Immuno plate (Fisher Scientific). Wells were coated for 1 h at 37° C., followed by overnight at 4° C., washed three times with wash buffer (PBS containing 0.05% TWEEN 20), and then blocked in wash buffer containing 1% bovine serum albumin (BSA) (Sigma) for 2 h at 37° C. Two-fold serial dilutions of each serum sample diluted in wash buffer containing 1% BSA ($1/64$ to $1/65,536$) were incubated in separate wells for 2 h at 37° C. and then washed three times in wash buffer. Wells were incubated with goat anti-chicken IgY horseradish peroxidase (HRP)-conjugated polyclonal antibody, diluted 1:5,000 in wash buffer for 1 h at room temperature, and then washed three times in wash buffer. Substrate solution (0.2 mg/ml 2,2'-azino-bis(3-ethylbenzothiazoline-6-sulphonic acid (ABTS) (Sigma) in 1× ABTS buffer (Sigma)) was added to each well and incubated for 30 min at room temperature. After the reaction was stopped with 0.5% sodium dodecyl sulfate (SDS), the absorbance was measured in a BioTek™ plate reader at 405 nm. Titers were calculated as the $\log_2$ value of the lowest serum dilution with an absorbance greater than twice that of the background wells, in which PBS containing 1% BSA was used in place of serum. Statistical differences between pre-immune and post-immune titers for each antigen among the different vaccination groups were determined by one-way ANOVA followed by Tukey's post-hoc test.

Figure 3A:
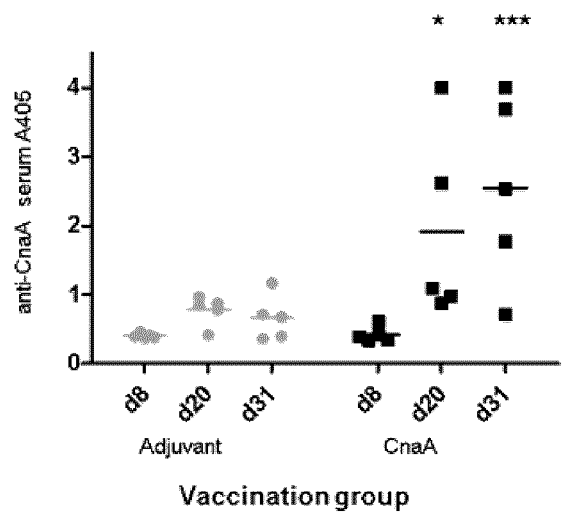
FIG. 3A is a graph illustrating serum IgY antibody response (absorbance at 405 nm) against CnaA recombinant polypeptide from chickens immunized with adjuvant alone, or with CnaA in a first vaccination trial. Each dot represents a single individual and horizontal lines represent means. * indicates a significant difference from the pre-immune sample (d8) from each group at the $p<0.05$ level,  indicates a significant difference at the $p<0.01$ level, and * indicates a significant difference at the $p<0.001$ level when measured by the Tukey's test (Tukey, J. "Comparing Individual Means in the Analysis of Variance". *Biometrics* (1949) 5(2): 99-114)
Figure 3B:
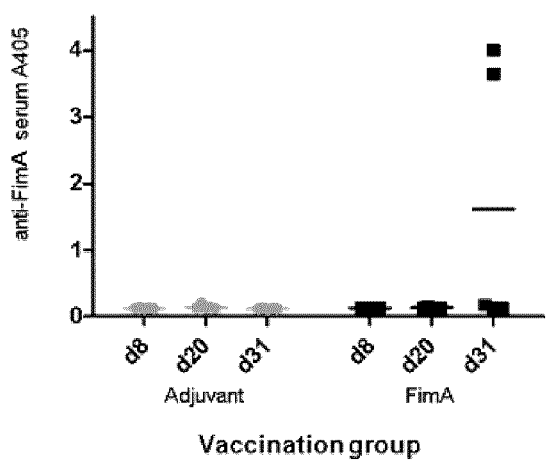
FIG. 3B is a graph illustrating serum IgY antibody response (absorbance at 405 nm) against FimA recombinant polypeptide from birds immunized with adjuvant alone, or with FimA in the trial of FIG. 3A. Each dot represents a single individual and horizontal lines represent means. * indicates a significant difference from the pre-immune sample (d8) from each group at the $p<0.05$ level,  indicates a significant difference at the $p<0.01$ level, and * indicates a significant difference at the $p<0.001$ level when measured by the Tukey's test.

The results are shown in FIGS. 3A and B, respectively. The average serum response against CnaA in the CnaA-immunized group was significantly higher at d31 compared to the pre-immune birds (d8), however the overall increase was small. In the FimA-immunized group, the average response against FimA did not significantly increase after immunization. However, two of the birds did exhibit a high titre by d31.

Birds were fed an antibiotic-free starter ration containing 20% protein until experimental induction of necrotic enteritis (NE). At day 27, birds were fasted for 24 h, and then switched to an antibiotic-free turkey starter ration (28% protein) containing *C. perfringens* CP1 culture at days 28 and 29 prior to euthanasia on day 31. The infected ration was prepared daily in the morning and afternoon by mixing with *C. perfringens* CP1 culture, grown in fluid thioglycollate (FTG) (Difco) medium at 37° C. for 15 h or 24 h, respectively, at a 2:1 (v/w) ratio. Following euthanasia, the small intestine (duodenum to ileum) of the bird was examined grossly for necrotic enteritis lesions and scored blindly from 1 to 6 using the system described by Keyburn et al (Keyburn A L, Boyce J D, Vaz P, Bannam T L, Ford M E, Parker D, Di Rubbo A, Rood J I, Moore R J. 2008. NetB, a new toxin that is associated with avian necrotic enteritis caused by *Clostridium perfringens*. PLoS Pathog. 4:e26) as follows:

0, no gross lesions;
1, thin or friable walls;
2, focal necrosis or ulceration (1-5 foci);
3, focal necrosis or ulceration (6-15 foci);
4, focal necrosis or ulceration (16 or more foci);
5, patches of necrosis 2-3 cm long;
6, diffuse necrosis typical of field cases.

Figure 4:
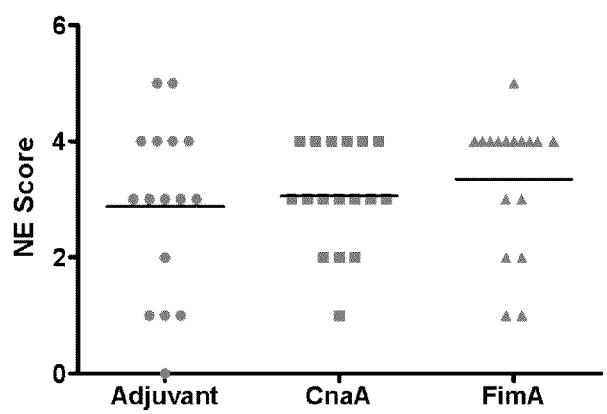
FIG. 4 is a graph illustrating necrotic enteritis (NE) lesion scores from groups of chickens immunized with adjuvant alone, or with CnaA or FimA in the trial of FIG. 3A, followed by in-feed challenge with *Clostridium perfringens* strain CP1. Each dot represents a single individual and horizontal lines represent mean necrotic enteritis lesion score.

Statistical differences between necrotic enteritis (NE) scores among groups were determined by one-way ANOVA (analysis of variance) followed by Tukey's post-hoc test. The results, shown in FIG. 4, indicate that all groups had similarly high average lesion scores. The average necrotic enteritis scores for the adjuvant-only control, CnaA-immunized and FimA-immunized groups were 3.1, 3.0 and 3.3, respectively.

Without being bound by theory, it is contemplated that the immunization at day 8 may have been subject to interference from maternal antibodies, and there may not have been time for the immunization at day 20 to elicit sufficient immune response prior to challenge with *C. perfringens* CP1. Therefore, a second vaccination trial was carried out including an additional immunization prior to challenge with *C. perfringens* CP1.

Trial 2:

The second trial consisted of four groups of 18 birds vaccinated subcutaneously (s.c.) with either adjuvant-only control, CnaA, FimB or a combination of CnaA, FimA and FimB. In this trial, each bird was immunized subcutaneously with 50 μg of recombinant polypeptide combined with 50 μg of Quil-A™ adjuvant at days 7, 14 and 19, and serum was collected at days 7, 19 and 29 for measurement of antibody titres. Birds were challenged in-feed with *Clostridium perfringens* strain CP1 on days 26 and 27 as described for Trial 1, and on day 29, birds were euthanized and intestinal lesions were scored.

Figure 5A:
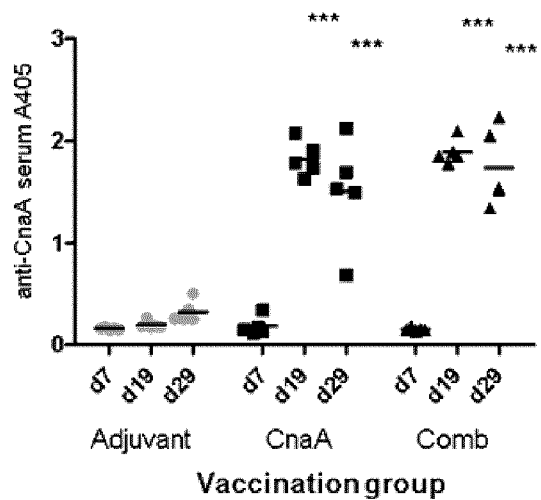
FIG. 5A is a graph illustrating serum IgY antibody response (absorbance at 405 nm) against CnaA recombinant polypeptide from chickens immunized with adjuvant alone, with CnaA, or with a combination of CnaA, FimA and FimB (Comb), in a second vaccination trial. Each dot represents a single individual and horizontal lines represent means. * indicates a significant difference from the pre-immune sample (d7) from each group at the $p<0.05$ level,  indicates a significant difference at the $p<0.01$ level, and * indicates a significant difference at the $p<0.001$ level when measured by the Tukey's test.

A significant ($p<0.001$) serum antibody (IgY) response was observed at both days 19 and 29 in all of the immunized groups compared to the pre-immune controls (with the exception of the group immunized with FimB at day 19), and the magnitude of response was also much greater than in Trial 1. The results are shown in FIGS. 5A (anti-CnaA serum response), 5B (anti-FimA serum response) and 5C (anti-FimB serum response).

Figure 5B:
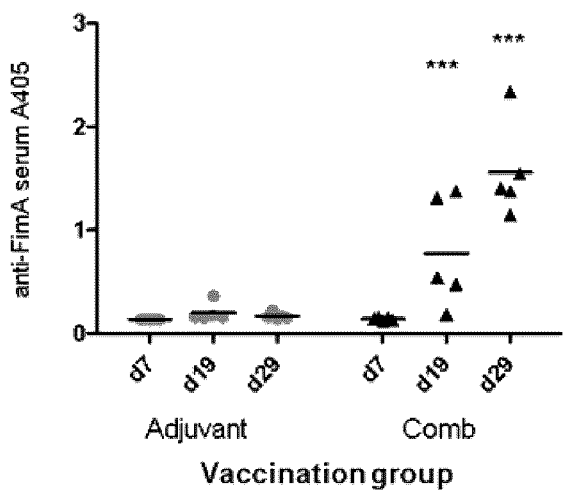
FIG. 5B is a graph illustrating serum IgY antibody response (absorbance at 405 nm) against FimA recombinant polypeptide from chickens immunized with adjuvant alone or with a combination of CnaA, FimA and FimB (Comb), in the trial of FIG. 5A. Each dot represents a single individual and horizontal lines represent means. * indicates a significant difference from the pre-immune sample (d7) from each group at the $p<0.05$ level,  indicates a significant difference at the $p<0.01$ level, and * indicates a significant difference at the $p<0.001$ level when measured by the Tukey's test.
Figure 5C:
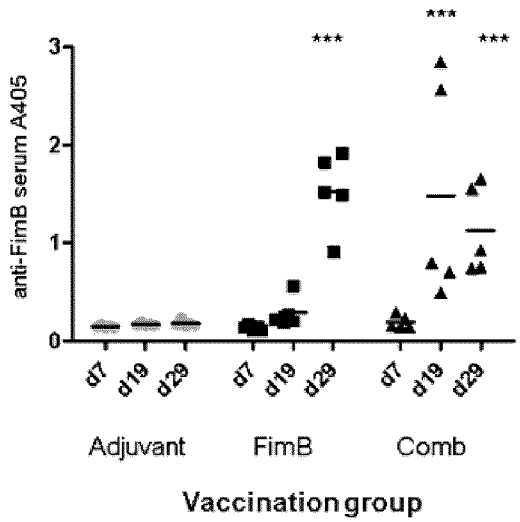
FIG. 5C is a graph illustrating serum IgY antibody response (absorbance at 405 nm) against FimB recombinant polypeptide from chickens immunized with adjuvant alone, with FimB, or with a combination of CnaA, FimA and FimB (Comb), in the trial of FIG. 5A. Each dot represents a single individual and horizontal lines represent means. * indicates a significant difference from the pre-immune sample (d7) from each group at the $p<0.05$ level,  indicates a significant difference at the $p<0.01$ level, and * indicates a significant difference at the $p<0.001$ level when measured by the Tukey's test.
Figure 6:
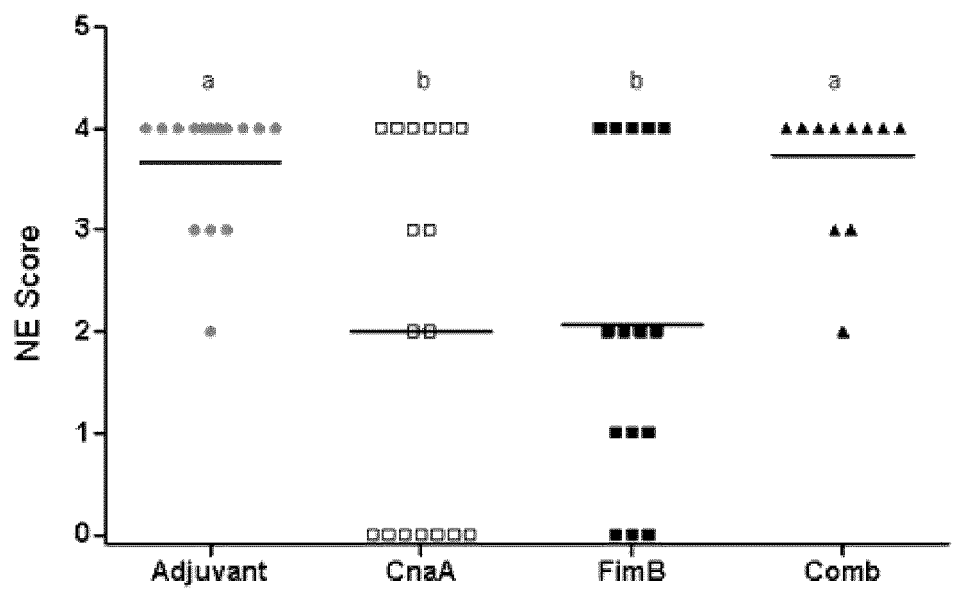
FIG. 6 is a graph illustrating necrotic enteritis (NE) lesion scores from groups of chickens immunized with adjuvant alone, CnaA, FimB, or a combination of CnaA, FimA and FimB (Comb), in the trial of FIG. 5A, followed by in-feed challenge with *Clostridium perfringens* CP1. Each dot represents a single individual and horizontal lines represent mean necrotic enteritis lesion score. Letters (a, b) denote significantly different groups (Tukey's; $p<0.01$)

In addition, as seen in FIG. 6, both the CnaA- and FimB-immunized groups had significantly lower necrotic enteritis scores (2 and 2.06, respectively) compared to the adjuvant control (3.75), when measured and scored as in Trial 1, indicating these antigens offered at least partial protection against necrotic enteritis. For the FimB antigen, the number of birds with severe disease (necrotic enteritis score>2) was 33.3% compared to 93.7% in the control. Immunization with the combined subunits did not appear to reduce the severity of disease (average necrotic enteritis score=3.7), despite eliciting a strong serum response against all three subunits, as seen in FIGS. 5A-C.

Figure 7:
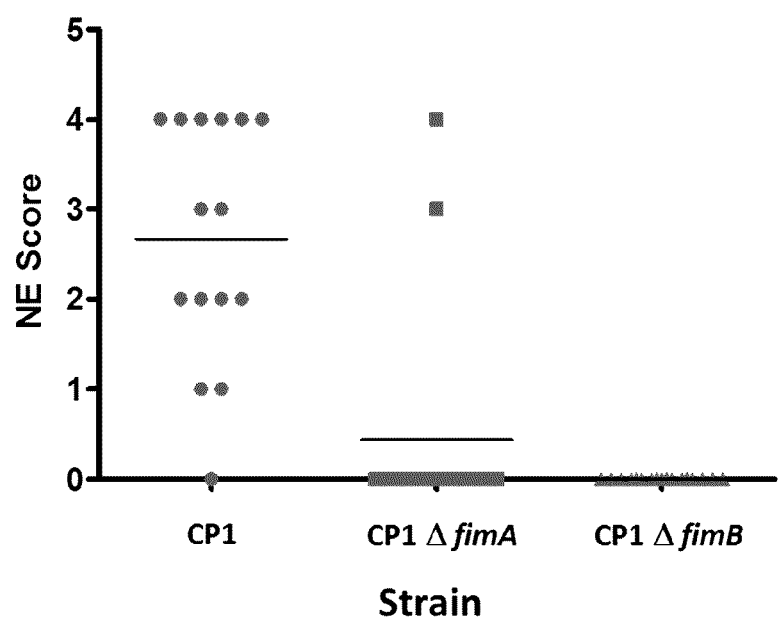
FIG. 7 is a graph illustrating necrotic enteritis (NE) lesion scores from groups of chickens following in-feed challenge with *Clostridium perfringens* strain CP1 or CP1 null-mutants of the pilus subunit genes fimA and fimB (CP1ΔfimA, and CP1ΔfimB). Lines represent mean necrotic enteritis lesion score.

Challenge of Chickens with *Clostridium perfringens* Strain CP1 Pilus Subunit Null-Mutants Three groups of 18 birds in Trial 2 which had not been immunized were challenged in-feed twice daily on days 26 and 27 with CP1, CP1ΔfimA or CP1ΔfimB prepared as described in Example 2. On day 29, the birds were euthanized and necrotic enteritis lesions were scored as described in Example 3. As seen from the results presented in FIG. 7, neither the CP1ΔfimA nor the CP1ΔfimB mutant strain caused disease in the challenged birds, indicating that a functional pilus appears to be required for necrotic enteritis pathogenesis.

Example 4: Characterization of *Clostridium perfringens* Pilus Surface Polypeptides

*Clostridium perfringens* Strain CP1 and CP1 Pilus Subunit Mutants:

Surface polypeptides were extracted from *Clostridium perfringens* strain CP1 and the pilus subunit mutants CP1ΔcnaA, CP1ΔfimA and CP1ΔfimB described in Example 3, using the method of Chang, C., Huang, I.-H., Hendrickx, A. P. A., Ton-That, H. 2013. Visualization of Gram-positive Bacterial Pili, In: Delcour, H. A. (Ed.) Bacterial Cell Surfaces: Methods and Protocols. Humana Press, Totowa, N.J., 77-95. Strains were grown overnight in TGY medium (3% tryptone, 2% glucose, 1% yeast extract) anaerobically at 37° C., subcultured 1:100 into 10 ml TGY medium and grown to an $OD_{600}$~1. Cells were pelleted at 6,000×g for 5 min and washed once in SMM buffer, pH 6.8 (0.5M sucrose, 10 mM $MgCl_2$, 10 mM maleate). The bacterial pellet was resuspended in 1 ml SMM buffer, to which was added 60 μl of 5 U/μl of mutanolysin (Sigma) in muramidase buffer (2 mM acetic acid, 48 mM sodium acetate) and 10 μl of 0.1M phenylmethylsulfonyl fluoride (PMSF) (Sigma). Following at least 4 h incubation at 37° C. with constant rotation, protoplasts were pelleted at 20,000×g for 5 min, and the supernatant fraction containing cell wall proteins was removed. Proteins were precipitated by addition of 81 μl 100% (w/v) trichloroacetic acid (TCA) (Sigma) per ml and incubation at 4° C. overnight. Following centrifugation at 20,000×g at 4° C. for 20 min, the protein pellet was washed with acetone and slowly resuspended in 50 μl sample loading buffer (62.5 mM Tris-HCl, pH 6.8, 2% SDS, 20% glycerol, 4% β-mercaptoethanol, 3M urea, 0.01% bromophenol blue) at room temperature for at least 15 min.

Surface protein extracts (5 μl) were loaded onto Novex™ NuPAGE™ 3-8% Tris-Acetate gels (Fisher Scientific) and electrophoresed at 150V for 1 h. Gels were stained with Bio-Safe™ COOMASSIE stain (BioRad), or were transferred onto a polyvinylene difluoride (PVDF) membrane at 350V for 1 h in 1× transfer buffer (48 mM Tris, 39 mM glycine, 20% methanol, 0.1% SDS). Chemiluminescent detection was performed with the WesternBreeze™ Chemiluminescent kit (Life Technologies) according to the manufacturer's instructions, using chicken anti-FimA serum (1:200) as primary antibody, and a goat anti-chicken IgY alkaline phosphatase (AP)-conjugated secondary antibody (1:2,000). The serum used as primary Ab was obtained at sacrifice from a FimA-immunized chicken from Trial 1 (Example 3) that subsequently exhibited a high anti-FimA titer or polyclonal antibodies raised in rabbits against the recombinant pilus polypeptides described in Example 1. The results are shown in FIGS. 8A-C.

It is known that Western blot analysis of SDS-PAGE separated sortase-dependent pili can produce a high-molecular weight (HMW) ladder-like pattern reflecting different polymer lengths, reflective of the mechanism by which the pilus is assembled at the cell surface. Pilin subunits are covalently linked by housekeeping and pilin-specific sortase enzymes, resulting in a growing heteropolymeric structure, which is eventually covalently linked to the cell wall peptidoglycan. The termination of assembly, and hence polymer length, is variable, giving rise to a characteristic high molecular weight ladder-like pattern when these pili are visualized by Western blotting. As seen in FIGS. 8B and C, a ladder-like pattern indicative of a pilus structure was observed in a Western blot of surface polypeptides extracted from *Clostridium perfringens* strain CP1 but not in a corresponding Western blot of surface polypeptides extracted from the mutant strains, whether visualized with antibodies obtained from chicken serum or raised in rabbits.

Various *Clostridium perfringens* Strains:

Extraction of surface polypeptides from five *C. perfringens* isolates that originated from poultry (CP1, JGS4141 and JGS4120) or non-poultry (Strain 13, ATCC13124) sources was performed as described above. Surface protein extracts (5 μl) were loaded onto two Novex™ NuPAGE™ 3-8% Tris-Acetate gels (Fisher Scientific) and electrophoresed at 150V for 1 h. One gel was used for staining with Bio-Safe™ COOMASSIE stain (BioRad), and the second gel was transferred onto a polyvinylene difluoride (PVDF) membrane at 350V for 1 h in 1× transfer buffer (48 mM Tris, 39 mM glycine, 20% methanol, 0.1% SDS). Chemiluminescent detection was performed with the WesternBreeze™ Chemiluminescent kit (Life Technologies) according to the manufacturer's instructions, using chicken anti-FimA serum (1:200) as primary antibody, and a goat anti-chicken IgY alkaline phosphatase (AP)-conjugated secondary antibody (1:2,000). The serum used as primary Ab was obtained at sacrifice from a FimA-immunized chicken that subsequently exhibited a high anti-FimA titer.

The results are shown in FIGS. 9A-B. The presence (+) or absence (−) of the genetic locus (VR-10B (CA) locus) for the pilus subunit genes cnaA, fimA and fimB in each *Clostridium perfringens* strain had previously been determined by both microarray analysis and polymerase chain reaction (PCR) methodology (Lepp D et al, *Journal of Bacteriology* (2013) 195: 1152-1166). As seen in FIGS. 9A-B, strains which carry the pilus genetic locus in their genomes (JGS4141 and CP1) showed the characteristic ladder-like pattern of a pilus structure in extracted surface polypeptides (indicated by the vertical line to the right of the gel image in FIG. 9B), when the Western blot was visualized with chicken anti-FimA antibody, while other strains which do not carry the pilus genetic locus in their genome do not show this pattern. Visualization of smaller molecular weight bands in the extracts are likely due to unrelated antibodies present in the crude chicken serum. None of the extracts showed a band corresponding to the FimA polypeptide itself, whose expected location is indicated by an arrow to the right of the gel image in FIG. 9B. This is not surprising, as surface-associated proteins would not be expected to include the FimA monomer, which is only found within cells.

Figure 10:
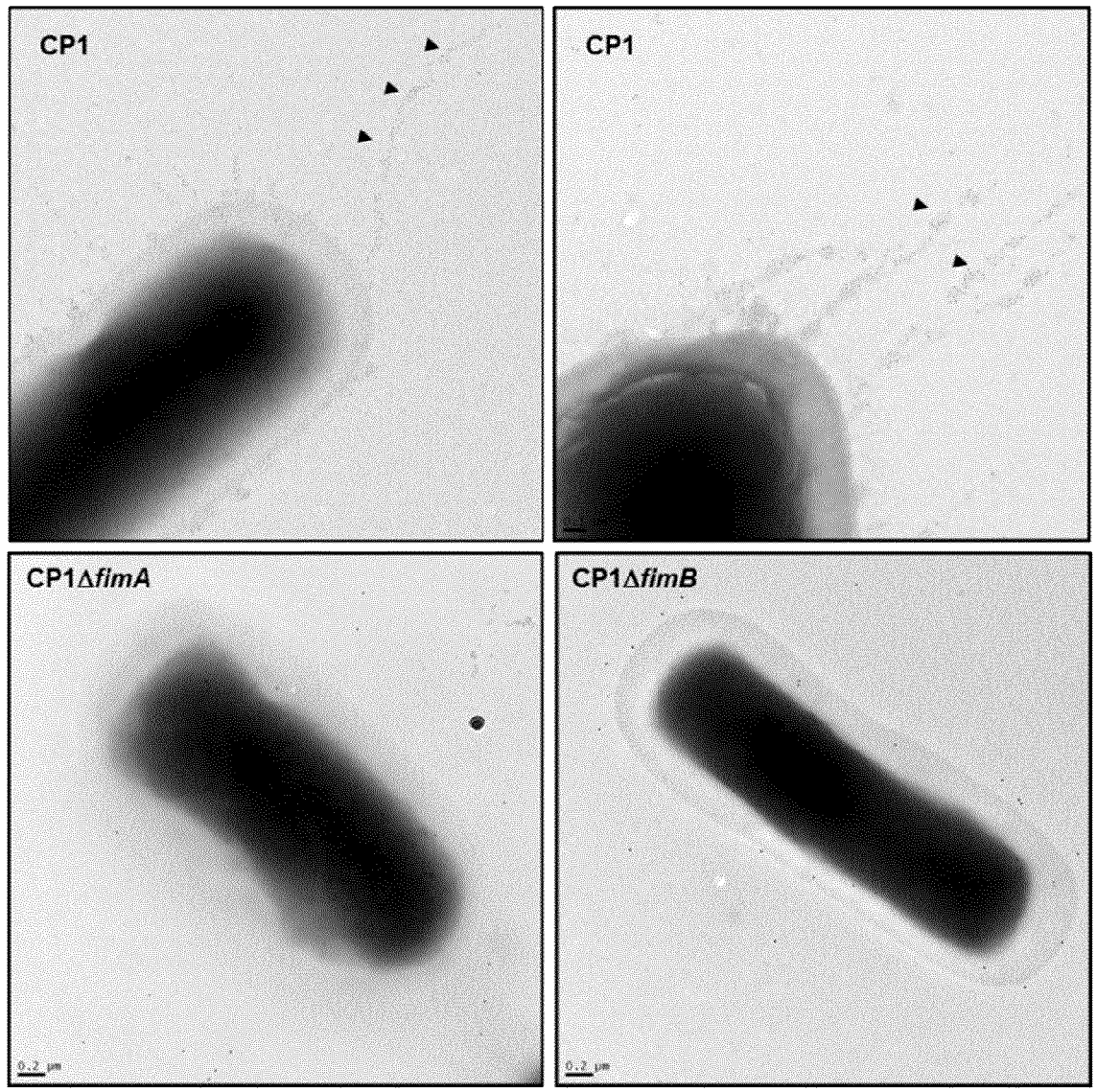

Immunogold Labeling of Clostridium perfringens Strain CP1 and CP1 Pilus Subunit Mutants:

Cells of Clostridium perfringens strain CP1 or of the CP1 null mutants CP1ΔfimA, and CP1ΔfimB were labeled with gold particles using an immunogold technique including rabbit anti-FimA as a primary antibody and 6 nm Colloidal Gold-AffiniPure™ Goat Anti-Rabbit IgG (H+L) (min X Hu,Ms,Rat Sr Prot) (Cedarlane) as secondary antibody, and examined by transmission electron microscopy, essentially as described previously (Chang, C., Huang, I.-H., Hendrickx, A. P. A., Ton-That, H. 2013. Visualization of Gram-positive Bacterial Pili, In: Delcour, H. A. (Ed.) Bacterial Cell Surfaces: Methods and Protocols. Humana Press, Totowa, N.J., 77-95). As seen in FIG. 10, cells of the native CP1 strain show the presence of a pilus structure on the cell surface, while cells of the CP1ΔfimA, and CP1ΔfimB mutants lack such structures.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

The invention claimed is:

1. An isolated *Clostridium perfringens* pilus polypeptide, wherein the pilus polypeptide is an assembled sortase-dependent pilus or a subunit thereof, wherein the subunit is a CnaA polypeptide comprising the amino acid sequence of SEQ ID NO: 13.

2. The isolated *Clostridium perfringens* pilus polypeptide according to claim 1, wherein the pilus polypeptide is the assembled sortase-dependent pilus.

3. An immunogenic polypeptide selected from the isolated *Clostridium perfringens* pilus polypeptide according to claim 1 and an isolated polypeptide variant thereof, wherein the pilus polypeptide and the variant are immunogenic in poultry and wherein the variant has at least 95% sequence identity to the pilus polypeptide.

4. The immunogenic polypeptide according to claim 3, wherein the variant has at least 99% sequence identity to the pilus polypeptide.

5. A vaccine for use in poultry against *Clostridium perfringens*, the vaccine comprising at least one of the immunogenic polypeptides according to claim 3.

6. A composition comprising the isolated *Clostridium perfringens* pilus polypeptide according to claim 1 and a pharmaceutically acceptable carrier.

7. A method of immunizing a subject, the method comprising administering an effective amount of the isolated *Clostridium perfringens* pilus polypeptide according to claim 1 to the subject.

8. The method according to claim 7, the subject being poultry.

9. A method of immunizing a subject, the method comprising administering an effective amount of the composition according to claim 6 to the subject.

10. The method according to claim 9, the subject being poultry.

11. The method according to claim 7, wherein the immunization is effective against *Clostridium perfringens* in poultry.

12. The vaccine according to claim 5, wherein the vaccine is for use against necrotic enteritis or *Clostridium perfringens* infection in the poultry.

13. The method according to claim 11, wherein the immunization is effective against necrotic enteritis or *Clostridium perfringens* infection in the poultry.

* * * * *